US008053571B2

(12) United States Patent
Johnson et al.

(10) Patent No.: US 8,053,571 B2
(45) Date of Patent: Nov. 8, 2011

(54) METHODS, COMPOSITIONS, AND APPARATUSES FOR FORMING MACROCYCLIC COMPOUNDS

(76) Inventors: Thomas E. Johnson, Athens, GA (US); Billy T. Fowler, Hull, GA (US)

( * ) Notice: Subject to any disclaimer, the term of this patent is extended or adjusted under 35 U.S.C. 154(b) by 0 days.

(21) Appl. No.: 12/772,749

(22) Filed: May 3, 2010

(65) Prior Publication Data

US 2010/0216970 A1     Aug. 26, 2010

Related U.S. Application Data

(63) Continuation of application No. 11/059,796, filed on Feb. 17, 2005, now Pat. No. 7,709,632.

(60) Provisional application No. 60/545,131, filed on Feb. 17, 2004.

(51) Int. Cl.
    C07B 47/00     (2006.01)
    C07D 487/22     (2006.01)

(52) U.S. Cl. ..................................... 540/145

(58) Field of Classification Search ................... 540/145
See application file for complete search history.

(56) References Cited

U.S. PATENT DOCUMENTS

| | | |
|---|---|---|
| 4,980,453 A | 12/1990 | Brunelle et al. |
| 5,206,362 A | 4/1993 | Speranza et al. |
| 5,214,158 A | 5/1993 | Brunelle et al. |
| 5,231,161 A | 7/1993 | Brunelle et al. |
| 5,357,029 A | 10/1994 | Takekoshi et al. |
| 5,512,675 A | 4/1996 | Tang et al. |
| 5,587,451 A | 12/1996 | Athey et al. |
| 5,936,100 A | 8/1999 | Furstner et al. |
| 5,948,693 A | 9/1999 | Rich et al. |
| 5,955,603 A | 9/1999 | Therien et al. |
| 6,072,054 A | 6/2000 | Abd-El-Aziz et al. |
| 6,080,826 A | 6/2000 | Grubbs et al. |
| 6,130,330 A | 10/2000 | Nestler et al. |
| 6,187,568 B1 | 2/2001 | Nishida et al. |
| 6,310,180 B1 | 10/2001 | Tam |
| 6,333,391 B1 | 12/2001 | Laycock et al. |
| 6,337,395 B1 | 1/2002 | Ercolani et al. |
| 6,433,162 B1 | 8/2002 | Nickel et al. |
| 6,610,351 B2 | 8/2003 | Shchegolikhin et al. |
| 6,712,972 B2 | 3/2004 | Pothuri et al. |
| 6,762,315 B1 | 7/2004 | Scherer et al. |
| 6,822,092 B2 | 11/2004 | Osuka |
| 6,849,730 B2 | 2/2005 | Lindsey et al. |
| 6,855,798 B2 | 2/2005 | Faler |
| 7,709,632 B2 | 5/2010 | Johnson et al. |
| 2002/0037560 A1 | 3/2002 | Chappell et al. |
| 2002/0137924 A1 | 9/2002 | Robinson et al. |
| 2004/0115724 A1 | 6/2004 | Lowik et al. |
| 2004/0132934 A1 | 7/2004 | Grubbs et al. |
| 2004/0206940 A1 | 10/2004 | Boschetti et al. |
| 2005/0096475 A1 | 5/2005 | Ikemoto et al. |

FOREIGN PATENT DOCUMENTS

| | | |
|---|---|---|
| EP | 0282455 A2 | 9/1988 |
| JP | 2000-016955 A | 1/2000 |
| JP | 2000-053675 A | 2/2000 |
| JP | 2000-191574 A | 7/2000 |

OTHER PUBLICATIONS

Korshak, V. et al. , "The Equilibrium Polycondensation", 1968, pp. 1-61, Publisher: Publishing house Nauka.
Lindsey, J. et al., "Rothemund and Adler-Longo Reactions Revisited: Synthesis of Tetraphenylporphyrins Under Equilibrium Conditions", "J. Org. Chem.", 1987, pp. 827-836, vol. 52.
Mishchenko, G. et al. , "Synthetic Methods Organic Chemistry Reference Book", "Chemistry", 1982, pp. 1-23.
Sharghi, H. et al. , "Novel Synthesis of meso-tetraarylporphyrins using $CF_3SO_2Cl$ under aerobic oxidation", "Tetrahedron", 2004, pp. 1863-1868, vol. 60, Publisher: Elsevier.
Adler, A.D., et al., "A Simplified Synthesis for meso-Tetraphenylporphyrin", J. Org. Chem., vol. 32, 1967, p. 476.
Algarra, F., et al., "Condensation of Pyrrole with Aldehydes in the Presence of Y Zeolites and Mesoporous MCM-41 Aluminosilicate: On the Encapsulation of Porphyrin Precursors", New J. Chem, 1998, pp. 333-338.
Amabilino, D.B., et al., "Interlocked and Intertwined Structures and Superstructures", Chem. Rev. vol. 95, 1995, pp. 2725-2828.
Baker, M.V., et al., "Rapid Communication. Imidazolium-Linked Cyclophanes", Aust. J. Chem., vol. 52 , 1999, pp. 823-825.
Balueva, A.S., et al., "Self-Assembly of Novel Macrocyclic Aminomethylphosphines with Hydrophobic Intramolecular Cavities", J. Chem. Soc. Dalton Trans., 2004, pp. 442-447.
Basak, A., et al., "Chelation-Controlled Bergamn Cyclization: Synthesis and Reactivity of Enediynyl Ligands", Chem. Rev., vol. 103, 2003, pp. 4077-4094.
Baxter, I., et al., "Macrocyclic Aromatic Thioether Sulfones", Chem. Commun. , 1998, pp. 283-284.
Ben-Haida, A., et al., "Cyclic Oligomers of Poly(ether ketone) (PEK): Synthesis, Extraction from Polymer, Fractionation and Characterization of the Cyclic Trimer, Tetramer and Pentamer", J. Mater. Chem., vol. 10, 2000, pp. 2011-2016.

(Continued)

Primary Examiner — Paul V. Ward
(74) Attorney, Agent, or Firm — David Bradin; Hultquist IP

(57) ABSTRACT

This invention relates to methods, compositions, and apparatuses for producing macrocyclic compounds. First, one or more reactants are provided in a reaction medium, which are capable of forming the macrocyclic compound through a desired reaction pathway that includes at least cyclization, and which are further capable of forming undesired oligomers through a undesired reaction pathway that includes undesirable oligomerization. Oligomerization of such reactions in the reaction medium is modulated to reduce formation of undesired oligomers and/or to reduce separation of the undesired oligomers from the reaction medium, relative to a corresponding unmodulated oligomerization reaction, thereby maximizing yields of the macrocyclic compound. The macrocyclic compound so formed is then recovered from the reaction medium. Preferably, the macrocyclic compound spontaneously separates from the reaction medium via phase separation. More preferably, the macrocyclic compound spontaneous precipitates from the reaction medium and therefore can be easily recovered by simple filtration.

11 Claims, 24 Drawing Sheets

OTHER PUBLICATIONS

Bonar-Law, R.P., "Porphyrin Synthesis in Surfactant Solution: Multicomponent Assembly in Micelles", J. Org. Chem., vol. 61, 1996, pp. 3623-3634.

Brückner, C. et al., "510-Diphenyltripyrrane A Useful Building Block for the Synthesis of meso-Phenyl Substituted Expanded Macrocycles", Chem. Commun., 1997, pp. 1689-1690.

Caminade A.-M. et al., "Synthesis of Phosphorus-Containing Macrocycles and Cryptands", Chem. Rev., vol. 94, 1994, pp. 1183-1213.

Cantrill S.J. et al.,"Nanoscale Borromean Rings", Accts. Chem. Res., vol. 38, 2005, pp. 1-9.

Cardona V.M.F. et al.,"Synthesis of Cyclic Peptides from Unprotected Precursors Using Removable N(alpha)-(1-(4-methoxyphenyl)-2-mercaptoethyl) Auxiliary", J. Peptide Res., vol. 61, 2003, pp. 152-157.

Caruso T. et al.,"Temperature Regiocontrol of Intramolecular Cyclization of Di-Hydroxysecoacids", Org. Biomol. Chem. vol. 2, 2004, pp. 3425-3426.

Chen C.-C. et al., "Ring-Chain Equilibrium in Reversibly Associated Polymer Solutions: Monte Carlo Simulations", Macromolecules, vol. 37, 2004, pp. 3905-3917.

Christinat N. et al., "A New method for the Synthesis of Boronate Macrocycles", Chem. Commun. ,2004, pp. 1158-1159.

Crossley M.J. et al.,"A Convenient Procedure for Moderate-Scale Rothemund Synthesis of Lipophilic Porphyrins: An Alternative to the Adler-Longo and Lindsey Methodologies" ,J. Porphyrins Phthalocyanines ,vol. 2.,1998, pp. 511-516.

Dawson P.E. et al., "Modulation of Reactivity in Native Chemical Ligation through the Use of Thiol Additives", J. Am. Chem. Soc., vol. 119 ,1997, pp. 4325-4329.

Deiters A. et al.,"Synthesis of Oxygen- and Nitrogen-Containing Heterocycles by Ring-Closing Metathesis", Chem. Rev. vol. 104, 2004, pp. 2199-2238.

Dietrich-Buchecker C.O. et al., "Interlocking of Molecular Threads: From the Statistical Approach to the Templated Synthesis of Catenands", Chem. Rev. vol. 87 (1987) pp. 795-810.

Edmonds D.J. et al., "Samarium(II)-Iodide-Mediated Cyclizations in Natural Product Synthesis", Chem. Rev., vol. 104, 2004, pp. 3371-3403.

Ercolani G. et al., "Macrocyclization Under Thermodynamic Control. A Theoretical Study and Its Application to the Equilibrium Cyclooligomerization of beta-Propiolactone", J. Am. Chem. Soc., vol. 115, 1993, pp. 3901-3908.

Franck B. et al., "Novel Porphyrinoids for Chemistry and Medicine by Biomimetic Syntheses", Angew. Chem. Int. Ed. Engl. vol. 34, 1995, pp. 1795-1811.

Faul M.M. et al. ,"Cyclization Strategies for the Synthesis of Macrocyclic Bisindolylmaleimides", J. Org. Chem. vol. 66,2001, pp. 2024-2033.

Fuchs B. et al., "Amplification of Dynamic Chiral Crown Ether Complexes During Cyclic Acetal Formation", Angew. Chem. Int. Ed., vol. 42, 2003, pp. 4220-4224.

Furlan, R.L.E. et al., "Supramolecular Templating in Thermodynamically Controlled Synthesis", Proc. Nat. Acad. Sci., vol. 99, 2002, pp. 4801-4804.

Gattuso G. et al., "Synthetic Cyclic Oligosaccharides", Chem. Rev., vol. 98, 1998, pp. 1919-1958.

Georgakilas V. et al., "Clays as a Host Matrix in the Synthesis of Organic Macrocycles", Chem. Eur. J., vol. 9, 2003, pp. 3904-3908.

Gonzalez-Alvarez A. et al., "Selective Host Amplification from a Dynamic Combinatorial Library of Oligoimines for the Synthesis of Different Optically Active Polyazamacrocycles", Eur. J. Org. Chem., 2004, pp. 1117-1127.

Gradillas A. et al., "Novel Synthesis of 5101520-Tetraarylporphyrins Using High-Valent Transition Metal Salts", J. Chem. Soc. Perkin Trans. 1, 1995, pp. 2611-2613.

Grubbs R.H. et al., "Ring-Closing Metathesis and Related Processes in Organic Synthesis", Acc. Chem. Res., vol. 28 1995, pp. 446-452.

Hall A.J. et al., "Synthesis of a Series of Cyclic Oligo(alkylidene isophthalate)s by Cyclo-Depolymerisation", Polymer ,vol. 41 ,2000, pp. 1239-1249.

Harvey D.F. et al., "Carbene-Alkyne-Alkene Cyclization Reactions", Chem. Rev., vol. 96 ,1996 ,pp. 271-288.

Heath R.E. et al. "Equilibrium Ring Concentrations and the Statistical Conformations of Polymer Chains: Part 16. Theoretical and Experimental Investigations of Cyclics Prepared from Poly(decamethylene fumarate) and Poly(decamethylene maleate) Ring-Chain Equilibrium Reactions", Polymer, vol. 41 ,2000, pp. 1487-1495.

Jacobson H. et al., "Intramolecular Reaction in Polycondensations. I. The Theory of Linear Systems" ,J. Chem. Phys., vol. 18 ,1950, pp. 1600-1607.

Jacobson H. et al.,"Intramolecular Reaction in Polycondensations .II. Ring Chain Equilibrium in Polydecamethylene Adipate", J. Chem. Phys., vol. 18 ,1950, pp. 1607-1612.

Janvier P. et al., "A One-Pot Four-Component (ABC2) Synthesis of Macrocycles", Angew. Chem. Int. Ed., vol. 42 ,2003,pp. 811-814.

Illuminati G. et al., "Ring Closure Reactions of Bifunctional Chain Molecules", Acc. Chem. Res. ,vol. 14, 1981 ,pp. 95-102.

Kantekin H. et al., "The Synthesis and Characterization of a Novel vic-Dioxime and its Mononuclear Complexes Bearing an 18-Membered N2O2S2 Macrocycle and their Characteristics as Extractants for Transition Metal Ions", J. Inc. Phenom. vol. 48, 2004, pp. 95-101.

Kieran A.L. et al., "Dynamic Combinatorial Libraries of Metalloporphyrins: Templated Amplification of Disulfide-Linked Oligomers", Chem. Commun., 2003, pp. 2674-2675.

Kieran A.L. et al., "Dynamic Synthesis of a Macrocycle Containing a Porphyrin and an Electron Donor", Chem. Commun., 2005, pp. 1842-1844.

Kohli R.M. et al., "Biomimetic Synthesis and Optimization of Cyclic Peptide Antibiotics", Nature ,vol. 418 ,2002 ,pp. 658-661.

Krakowiak K.E. et al., "One-Step Syntheses of Macrocyclic Compounds: A Short Review",J. Heterocyclic Chem., vol. 38 ,2001, pp. 1239-1248.

Kral V. et al., "Calixphyrins: Novel Macrocycles at the Intersection between Porphyrins and Calixpyrroles", Angew. Chem. Int., Ed. vol. vol. 39, 2000, pp. 1055-1058.

Kricheldorf H.R.,"Macrocyclic Dibutyltin Dicarboxylates via Thermodynamically Controlled Polycondensations", Macromol. Chem. Phys., vol. 203, 2002, pp. 313-318.

Kricheldorf H.R. et al., "Cyclic Polymers by Kinetically Controlled Step-Growth Polymerization", Macromol. Rapid Commun., vol. 24, 2003, pp. 359-381.

Lambert J.N. et al., "The Synthesis of Cyclic Peptides", J. Chem. Soc. Perkin Trans. 1, 2001, pp. 471-484.

Langer P. et al.,"Cyclization Reactions of Dianions in Organic Synthesis", Chem. Rev. vol. 104, 2004, pp. 4125-4149.

Lehn Jean-Marie, "Cryptates: The Chemistry of Macropolycyclic Inclusion Complexes", Acc. Chem. Res., vol. 11, 1978, pp. 49-57.

Leininger S. et al.,"Self-Assembly of Discrete Cyclic Nanostructures Mediated by Transition Metals", Chem. Rev., vol. 100, 2000, pp. 853-908.

Li, F., et al., "Beneficial Effects of Salts on an Acid-Catalyzed Condensation Leading to Porphyrin Formation", Tetrahedron, vol. 53, 1997, pp. 12339-12360.

J.L., et al.,"Rothemund and Adler-Longo Reactions Revisited: Synthesis of Tetraphenylporphyrins Under Equilibrium Conditions", Lindsey, J. Org. Chem. vol. 52, 1987, pp. 827-836.

Little, R. Daniel, "Diyl Trapping and Electoreductive Cyclization Reactions", Chem. Rev. vol. 96, 1996, pp. 93-114.

Lüning, U., "Synthesizing Macrocycles Under Thermodynamic Control-Dynamic Combinatorial Libraries and Templates", J. Inc. Phenom., vol. 49, 2004, pp. 81-84.

Kricheldorf H.R.,"Macrocycles. 21. Role of Ring—Ring Equilibria in Thermodynamically Controlled Polycondensations", Macromolecules, vol. 36, pp. 2302-2308, (2004).

McReynolds, M.D., et al., "Synthesis of Phosphorous and Sulfur Heterocycles via Ring-Closing Olefin Metathesis", Chem. Rev. vol. 104 (2004) pp. 2239-2258.

Meutermans, W.D.F., et al., "Difficult Macrocyclizations: New Strategies for Synthesizing Highly Strained Cyclic Tetrapeptides", Org. Lett. vol. 5 (2003) pp. 2711-2714.

Molander, Gary A., "Diverse Methods for Medium Ring Synthesis", Acc. Chem. Res. vol. 31 (1998), pp. 603-609.

Negishi, E.-i., et al., "Cyclic Carbopalladation. A Versatile Synthetic Methodology for the Construction of Cyclic Organic Compounds", Chem. Rev. vol. 96 (1996), pp. 365-393.

Newkome, G.R., et al., "Construction of Synthetic Macrocyclic Compounds Possessing Subheterocyclic Rings, Specifically Pyridine, Furan, and Thiophene", Chem. Rev. vol. 77 (1977), pp. 513-597.

Paolesse, R., et al., "Synthesis and Functionalization of meso-Aryl-Substituted Corroles", J. Org. Chem. vol. 66 (2001), pp. 550-556.

Rama Rao, A.V., et al., "Studies Directed Toward the Synthesis of Vancomycin and Related Cyclic Peptides", Chem. Rev. vol. 95 (1995), pp. 2135-2167.

Rao, M.L.N., et al., Novel Synthesis of Macrocycles with Chalcone Moieties through Mixed Aldol Reactio, Tetrahedron Lett. vol. 42 (2001), pp. 8351-8355.

Rowan, S.J., et al., "Building Thermodynamic Combinatorial Libraries of Quinine Macrocycles", Chem. Commun. (1997), pp. 1407-1408.

Rowan, S.J., et al., "Dynamic Covalent Chemistry", Angew. Chem. Int. Ed. vol. 41 (2002), pp. 898-952.

Royer, J., et al., "Chiral Heterocycles by Iminium Ion Cyclization", Chem. Rev. vol. 104 (2004), pp. 2311-2352.

Salavati-Niasari, M., et al., "Template Condensation Reactions of Formaldehyde with Amines and 2,3-Butanedihydrazone: Preparation and Properties of Nickel(II) Complexes of 18-Membered Decaaza Macrocycles", Polyhedron vol. 23 (2004), pp. 1325-1331.

Sauvage, Jean-Pierre, "Interlacing Molecular Threads on Transition Metals: Catenands, Catenates, and Knots", Acc. Chem. Res. vol. 23 (1990), pp. 319-327.

Schafer, L.L., "Efficient Diastereoselective Synthesis of Chiral Macrocycles via Zirconocene Coupling. Synthetic Control of Size and Geometry", J. Am. Chem. Soc. vol. 123, (2001), pp. 2683-2684.

Sessler, J.L., et al., "Synthetic Expanded Porphyrin Chemistry", Angew. Chem. Int. Ed. vol. 42 (2003), pp. 5134-5175.

Shanmugathasan, S., et al., "Advances in Modern Synthetic Porphyrin Chemistry", Tetrahedron vol. 56, (2000), pp. 1025-1046.

Sharghi, H., "Efficient Synthesis of Macrocyclic Diamides", Tetrahedron vol. 51 (1995), pp. 913-922.

Shimakoshi, H., et al., "Syntheses of Large-Membered Macrocycles Having Multiple Hydrogen Bonding Moieties", Tetrahedron Lett. vol. 43 (2002), pp. 8261-8264.

Roxburgh, C.J., "The Synthesis of Large Ring Compounds", Tetrahedron vol. 51 (1995), pp. 9767-9822.

Spence, J.D., et al., "Porphyrins with Exocyclic Rings. 14. Synthesis of Tetraacenaphthoporphyrins, a New Family of Highly Conjugated Porphyrins with Record-Breaking Long-Wavelength Electronic Absorptions", J. Org. Chem. vol. 65 (2000), pp. 1530-1539.

Storm, O., et al., "How to Synthesize Macrocycles Efficiently Using Virtual Combinatorial Libraries", Chem. Eur. J. vol. 8 2002, pp. 793-798.

Tam, J.P., et al., "A Biomimetic Strategy for the Synthesis and Fragmentation of Cyclic Protein", Protein Sci., vol. 7, 1998, pp. 1583-1592.

Tam, J.P., et al., "Thia Zip Reaction for Synthesis of Large Cyclic Peptides: Mechanisms and Applications", J. Am. Chem. Soc. vol. 121, 1999, pp. 4316-4324.

Tam, J.P., et al., "Orthogonal Ligation Strategies for Peptide and Protein", Biopolymers vol. 51, 1999, pp. 311-332.

Tripathy, N.K., et al., "RCM Approach for the Total Synthesis of Crytophycin-24 (Arenastatin A)", Tetrahedron Lett. vol. 45, 2004, pp. 5309-5311.

Vilar, R., "Anion-Templated Synthesis", Angew. Chem. Int. Ed., vol. 42, 2003, pp. 1460-1477.

Winnik, Mitchell A., "End-to-End Cyclization of Polymer Chains", Acc. Chem. Res., vol. 18 ,1985, pp. 73-79.

Yet, Larry, "Metal-Mediated Synthesis of Medium-Sized Rings", Chem. Rev., vol. 100, 2000, pp. 2963-3007.

Yuan, L., et al., "Highly Efficient, One-Step Macrocyclizations Assisted by the Folding and Preorganization of Precursor Oligomers", J. Am. Chem. Soc., vol. 126, 2004, pp. 11120-11121.

Zhang, L., et al., "Synthesis and Application of Unprotected Cyclic Peptides as Building Blocks for Peptide Dendrimers", J. Am. Chem. Soc., vol. 119 ,1997, pp. 2363-2370.

Zhang, L., et al., "Lactone and Lactam Library Synthesis by Silver Ion-Assisted Orthogonal Cyclization of Unprotected Peptides", J. Am. Chem. Soc., vol. 121, 1999, pp. 3311-3320.

Zhang, W., et al., "Arylene Ethynylene Macrocycles Prepared by Precipitation-Driven Alkyne Metathesis", J. Am. Chem. Soc., vol. 126 2004, p. 12796.

Sessler, J. et al., "Sapphyrins and Heterosapphyrins", "Tetrahedron", 1992, pp. 9661-9672, vol. 48, No. 44.

Sessler, J. et al., "Anion Binding: Self Assembly of Polypyrrolic Macrocycles", "Agnew. Chem. Int. Ed. Engl.", 1996, pp. 2782-2784, vol. 35, No. 23/24.

Li, F., et al., "Beneficial Effects of Salts on an Acid-Catalyzed Condensation Leading to Porphyrin Formation", "Tetrahedron", 1997, pp. 12339-12360, vol. 53, No. 37.

METHODS, COMPOSITIONS, AND APPARATUSES FOR FORMING MACROCYCLIC COMPOUNDS

CROSS REFERENCE TO RELATED APPLICATIONS

This application is a continuation of U.S. patent application Ser. No. 11/059,796 filed Feb. 17, 2005, issuing as U.S. Pat. No. 7,709,632 on May 4, 2010, which claims priority to U.S. Provisional Patent Application No. 60/545,131 filed Feb. 17, 2004. The disclosures of all of the foregoing applications are hereby incorporated herein by reference in their respective entireties, for all purposes, and the priority of all such applications is hereby claimed under the provisions of 35 U.S.C. §120.

FIELD OF THE INVENTION

The present invention relates generally to methods, compositions, and apparatuses for synthesizing a wide variety of macrocyclic compounds.

BACKGROUND OF THE INVENTION

At a time when the small-molecule pipeline of the pharmaceutical industry is beginning to run dry, the number of macrocycles has increased in an explosive manner. This fast-growing phenomenon is due to the discovery of an impressive number of new families of natural, semi-synthetic, and synthetic compounds, which possess extraordinary properties. The macrocyclic structure is a particularly desirable feature for the pharmaceutical industry. The cyclic structure stabilizes the molecule against destruction by the human body and increases its effectiveness in comparison with its linear analog, by constraining it to a biologically active form. Accordingly, macrocycles constitute a major class of pharmaceutical agents that are currently under wide-spread clinical investigation.

Moreover, macrocycles are key components in many other fields, including nanotechnology. Nanoscale devices such as chemical noses for the detection of land mines, sensors for the detection of chemical weapons, light rods for solar energy conversion, photovoltaic cells, light emitting diodes, magnetic materials, multi-bit storage devices, and semi-conducting materials have already been fashioned using macrocyclic compounds.

In spite of their great potential, however, macrocycles have remained relatively under-explored and unexploited. Current methods used for the preparation of macrocycles severely limit their use in medicine and other important industries. While some of these compounds are available from biological sources in quantities sufficient for basic research or initial clinical studies, others need to be produced by semi- or total synthesis. The present methodologies for producing macrocycles require hundreds of man-hours of work, produce large amounts of toxic waste, require expensive manufacturing facilities, and still produce frustratingly low quantities of the desired material. Low production yield renders the profit margins of these molecules too small for commercial production. Consequently, due to the high costs and low profit margins associated with production of macrocycles by conventional chemical manufacturing approaches, many important discoveries are not commercialized. More importantly, the staggering potential of macrocyclic research and development is largely unrealized, as the result of the inability of the art to provide a practical method for making such compounds.

Thus, the inability to obtain large quantities of macrocyclic molecules has been, and still is, the major stumbling block for their commercial exploitation, as well as the stimulus for efforts to improve existing methods or to discover new ones.

Conceptually, the synthesis of cyclic molecules begins with the preparation of open-chained starting materials which are cyclized by a ring closure reaction. In contrast to the efficient formation of five- or six-member rings, however, problems are encountered when cyclization of compounds of other sizes, both smaller and larger, is carried out in practice: yields of small rings (3-4 atoms) are low and even lower for medium rings (8-12 carbon atoms) and macrocycles (>12 atoms). Due to ring strain effects, small rings are less stable than five- or six-member rings, and thus they are more difficult to obtain. However, most macrocycles are unstrained and their enthalpy of formation is comparable to that of five- or six-member rings. Thus, there are no thermodynamic barriers to the formation of unstrained macrocycle. Nonetheless, the kinetics of the formation of macrocycles greatly complicates their formation. For entropic reasons, it is more difficult to synthesize macrocycles than small and medium ring compounds because macrocyclic ring formation involves a low probability for coincident positioning of the two ends of the open chain starting material, as required for cyclization to occur. Further, intermolecular reactions of the reactive ends of the linear precursor compete with the cyclization reaction. Such intermolecular reactions lead to formation of undesired oligomers and polymers.

In order to circumvent these undesirable oligomerization reactions, cyclization is generally carried out under relatively dilute conditions (typically less than 10 mM). The rationale for the high dilution synthesis method is that if the concentration of the reactants is sufficiently low, then the ring closure reaction will be favored, since the reactive ends thereby are isolated from the reactants and therefore more likely to react in an intramolecular fashion to effect ring formation. However, the high dilution principle is most effective if the cyclization reaction is an irreversible reaction and the rate of cyclization is greater than the rate of polymerization. In contrast to this kinetic approach, in a thermodynamically controlled, reversible reaction, the relative stabilities of all products, macrocyclic or acyclic, determine the product distribution. If the macrocycle is the most stable compound in such reversible reaction system, then the macrocycle will be formed in good yield. Indeed, some examples exist where macrocycles are in fact formed as the most stable products in a reversible reaction. However, in most cyclization reactions, macrocycles and undesired oligomers and polymers are of comparable thermodynamic stabilities and therefore, all of them will exist as a complex mixture, which requires extensive and complicated purification procedures in order to obtain the desired macrocyclic material. Furthermore, high dilution methods can only provide limited quantities of the macrocyclic material and are therefore inappropriate for high-volume commercial production.

In order to overcome or mediate the above-described difficulties and complications, a wide variety of modifications and improvements have been made to the high dilution methods, by adapting such methods to the individual requirements of specific target molecules. These approaches have achieved a wide variety of levels of success, on a molecule by molecule basis. For example, it is now possible to prepare modest quantities of certain macrocycles by appropriate choice of starting material, solvent, temperature, catalyst and dilution conditions, often with the assistance of other effects, e.g., the template effect, the rigid group principle, and other pseudo-dilution phenomenon.

In supramolecular chemistry, for example, the use of an appropriate template can greatly improve cyclization steps. For those examples where the building blocks for the macrocycle and its oligomers are the same, an organic or inorganic guest material (i.e., a template) may be found which binds complementarily into the cavity formed by the macrocycle. Under reversible conditions, the resulting supramolecular complex will be more stable than the macrocyclic component and thus favored, which is known as the template effect. In addition to mixtures in equilibrium, the template effect can also be useful in kinetically controlled reactions when the template facilitates the intramolecular reaction by pre-organizing the reactive ends. Important features in high yield template-assisted cyclization reactions include the geometry of the template material, and the number of heteroatoms in the interior cavity of the macrocycle that are available for coordinating with the template.

In addition to template materials that bind to a cavity formed by the macrocycle, other materials with microporous structures can pre-organize the reactive ends of the reactants and thereby facilitate the ring closure reaction, by providing a localized environment defined by the microporous structure that is highly favorable to the ring closure reaction. For example, Smectite clays have been used to provide substantial improvements in yield and/or selectivity of macrocyclic compounds. The predetermined architectures of the microporous structures in the clays can be effectively used to pre-organize the reactive substances in a manner that controls the extent of oligomerization and the geometry of the macrocycle so formed. Subsequently, the final macrocyclic product can be removed from the clay framework.

Further, some structural elements have emerged that show a propensity to bend linear structures and form pre-organized ring structures, suggesting that such pre-organization can be used to favor intramolecular processes over the intermolecular ones and provide simple routes for the preparation of macrocyclic structures. This predisposition of certain molecules to bending or folding has been widely studied, e.g., the Thorpe-Ingold effect, and several structural elements, such as urea and proline residues, have been identified as being associated with the formation of U-turns in natural products. Consequently, sterically encumbering groups can be added to acyclic precursors to effectuate bending thereof and to facilitate ring closure, when the target macrocyclic compound does not normally contain such sterically encumbering groups.

Recent years have witnessed a renaissance in the field of peptides. At present, more than 40 peptides are on the market, many more are in registration processing, hundreds are in clinical trials and more than 400 are in advanced preclinical studies. The enhanced biological specificity, activity, and metabolic stability of cyclopeptides in comparison with those of the linear peptides, as a result of the constrained structural features of the cyclic peptides, have attracted much attention. Cyclic peptidomimetic scaffolds and templates have been widely used to assemble a wide variety of spatially defined functional groups for molecular recognition and drug discovery. There is a vigorous, on-going effort to device and develop commercially applicable synthetic methods for preparation of cyclic peptides and peptidomimetics.

Cyclic peptides can be synthesized from partially protected linear precursors formed in solution or by solid-phase techniques involving cyclization of such linear precursors in solution under high or pseudo-dilution conditions. Alternatively, cyclic peptides can be prepared by solid-phase assembly of the linear peptide sequence, followed by cyclization while the peptide remains anchored to a polymeric support. This method takes advantage of the pseudo-dilution phenomenon attributed to the solid-phase, which favors intramolecular reactions over intermolecular side reactions. More recently, chemical ligation methods have also shown some success in the formation of cyclic peptides, specifically in the formation of backbone peptide bonds. Unlike other methods, chemical ligation methods do not require coupling reagents or protection schemes, but are achieved through a variable chemoselective capture step followed by an invariable intramolecular acyl transfer reaction.

Despite the development of the above-discussed synthesis techniques and other high-dilution or pseudo-dilution methods, however, the practical aspects of the synthesis principle, viz., the selection of starting materials and reaction parameters, still have to be determined empirically, and the cyclization step still remains as the fundamental synthetic challenge. The requirements for complex multi-step processes, specific reaction conditions, templates, selective protection/deprotection steps, and high dilution of the reaction materials continue to restrict commercial production of macrocyclic compounds, even after extensive optimization, and the modified or improved methods still suffer from many limitations of the original high-dilution procedure.

A general method that does not depend on high dilution of the reaction materials or otherwise suffer the deficiencies of high dilution techniques and is useful for synthesis of a wide variety of macrocyclic compounds on a commercial scale would be of immense value.

SUMMARY OF THE INVENTION

The present invention relates to a new method for producing macrocyclic compounds, which can be generally applied to increase the production yield and the volumetric production efficiency of a wide variety of different classes of macrocyclic compounds.

The present invention also relates to new compositions and to apparatuses for automated synthesis of a wide variety of macrocyclic compounds for scale-up commercial production of macrocyclic compounds at significantly reduced cost.

In one aspect, the present invention relates to a process for manufacturing at least one macrocyclic compound, which comprises the steps of: (a) providing a reaction system comprising one or more reactants in a reaction medium, wherein such reactants are capable of forming the macrocyclic compound in the reaction medium at a first set of reaction conditions through at least one desired reaction pathway that includes at least cyclization reaction(s), and wherein such reactants are further capable of forming undesired oligomers at the first set of reaction conditions through at least one undesired reaction pathway that includes undesirable oligomerization reactions; and (b) modulating oligomerization reactions of such one or more reactants in the reaction medium, so as to reduce formation of the undesired oligomers by such one or more reactants and/or to reduce separation of the undesired oligomers from the reaction medium, relative to corresponding unmodulated oligomerization reactions.

The present invention in another aspect relates to a process for manufacturing at least one macrocyclic compound, comprising the steps of: (a) providing a reaction system comprising one or more reactants in a reaction medium, wherein such reactants are capable of forming an intermediate macrocyclic compound in the reaction medium at a first set of reaction conditions through at least one desired reaction pathway that includes at least cyclization reaction(s), and wherein such reactants are further capable of forming undesired oligomers at the first set of reaction conditions through at least one undesired reaction pathway that includes undesirable oligomerization reactions; and (b) modulating oligomerization reactions of such one or more reactants in the reaction medium, so as to reduce formation of undesired oligomers by such one or more reactants and/or to reduce separation of the undesired oligomers from the reaction medium, relative to corresponding unmodulated oligomerization reactions; and (c) modifying the intermediate macrocyclic compound to form a macrocyclic compound of interest.

In a further aspect, the present invention relates to a reaction composition for forming a macrocyclic compound, comprising:

(1) one or more reactants, wherein such reactants are capable of forming the macrocyclic compound at a first set of reaction conditions through at least one desired reaction pathway that includes at least cyclization reaction(s), and wherein such reactants are further capable of forming undesired oligomers at the first set of reaction conditions through at least one undesired reaction pathway that includes undesirable oligomerization reactions;

(2) one or more reacting solvents for dissolving the reactants; and (3) one or more oligomerization control additives that modulate oligomerization reactions of such reactants by reducing formation of undesired oligomers and/or separation of the undesired oligomers from such reaction composition, relative to a corresponding reaction composition lacking such oligomerization control additive(s).

In a still further aspect, the present invention relates to a system for manufacturing at least one macrocyclic compound, comprising at lease one reaction zone having: (1) one or more supply vessels for supplying one or more reactants and/or one or more solvents, wherein such reactants are capable of forming the macrocyclic compound in a reaction medium comprising such one or more solvents at a first set of reaction conditions through at least one desired reaction pathway that includes at least cyclization reaction(s), and wherein such reactants are further capable of forming undesired oligomers at the first set of reaction conditions through at least one undesired reaction pathway that includes undesirable oligomerization reactions, (2) a reaction chamber coupled with such supply vessels for receiving the reactants and solvents and effectuating reactions of the reactants therein to form the macrocyclic compound, and (3) an oligomerization modulation unit for modulating oligomerization reactions of such one or more reactants in the reaction chamber, so as to reduce formation of undesired oligomers by such one or more reactants or to reduce separation of the undesired oligomers from the reaction medium, relative to corresponding unmodulated oligomerization reactions.

Another aspect of the present invention relates to a process for synthesizing a macrocyclic compound through cyclization reaction(s), including the use of an oligomerization control agent to control undesired oligomerization reactions that compete with said cyclization reaction(s).

Other aspects, features and embodiments of the invention will be more fully apparent from the ensuing disclosure and appended claims.

DEFINITIONS

The words "a" and "an" as used herein are not limited to their singular senses, but also covers the plural.

The phrases "macrocycles," "macrocyclic compounds," and "cyclic compounds" are used interchangeably herein to refer to both single cyclic and multi-cyclic compounds having one or more ring structures. The total number of atoms on each of such ring structures may be widely varied, e.g., in a range of from 3 to about 100 or more. Such single cyclic or multi-cyclic compound may further contain one or more linear functional groups, branched functional groups, and/or arched functional groups that bridge across a plane defined by a ring structure. In the case of multi-cyclic compounds having two or more ring structures, any pair of such ring structures may be separated from each another by a non-cyclic spacing structure, or the rings can be in side-by-side relationship to each another, sharing one chemical bond or one atom, or alternatively, the rings may partially overlap with each other, or one ring structure can be enclosed by or intertwined with the other ring. The three-dimensional structures of such compounds can be characterized by any geometric shape, either regular or irregular, including, but not limited to, planar, cylindrical, semispherical, spherical, ovoidal, helical, pyriamidyl, etc. Specifically, such macrocyclic compounds may include, but are not limited to porphyrinogens, porphyrins, saphyrins, texaphyrins, bacteriochlorins, chlorins, coproporphyrin I, corrins, corroles, cytoporphyrins, deuteroporphyrins, etioporphyrin I, etioporphyrin III, hematoporphyrins, pheophorbide a, pheophorbide b, phorbines, phthalocyanines, phyllochlorins, phylloporphyrins, phytochlorins, phytoporphyrins, protoporphyrins, pyrrochlorins, pyrroporphyrins, rhodochlorins, rhodoporphyrins, uroporphyrin I, calix[n]pyrroles, calix[n]erines, cycloalkanes, cycloalkenes, cycloalkynes, piperidines, morpholines, pyrrolidines, aziridines, anilines, thiophenes, quinolines, isoquinolines, naphthalenes, pyrimidines, purines, benzofurans, oxiranes, pyrroles, thiazides, ozazoles, imidazoles, indoles, furans, benzothiophenes, polyazamacrocycles, carbohydrates, acetals, crown ethers, cyclic anhydrides, lactams, lactones, cyclic peptides, phenylthiohydantoins, thiazolinones, succinimides, coronenes, macrolides, carbocyclics, cyclodextrins, squalene oxides, ionophore antibiotics, cyclic bis-N,O-acetals, cyclic disulfides, terpenoids, spirocycles, resorcinarene macrocycles, cyclic oligo(siloxane)s, stannylated cyclic oligo(ethyleneoxide)s, cyclic poly(dibutyltindicarboxylate)s, cyclic poly(pyrrole), cyclic poly(thiophene)s, cyclic poly(amide)s, cyclic poly(ether)s, cyclic poly(carbonate)s, cyclic poly(ethersulfone)s, cyclic poly(etherketone)s, cyclic poly(urethane)s, cyclic poly(imide)s, cyclic poly(decamethylene fumarate)s, cyclic poly(decamethylethylene maleate)s, etc.

The phrase "desired oligomer" as used herein refers to the oligomeric or polymeric compound formed by the reactants in the reaction composition of the present invention, which has the appropriate oligomer number (number of mer units) for forming the desired macrocyclic compound by cyclization reaction.

The phrase "desired oligomerization" as used herein refers to the oligomerization reaction(s) that form the desired oligomers.

The phrase "undesired oligomers" as used herein refers to a wide variety of oligomeric and/or polymeric compounds other than the desired oligomer, which are also formed by the reactants in the reaction composition of the present invention, and which have oligomeric or polymeric numbers (number of mer units) that are either smaller or larger than that of the desired oligomer.

The phrase "undesired oligomerization" as used herein refers to the oligomerization reactions that form the undesired oligomers.

The phrase "modulating" or "modulation" as used herein in reference to oligomerization reactions is intended to be broadly construed, to encompass any type of intervention affecting the oligomerization reactions to cause reduction in formation of the undesired oligomers and/or separation of the already formed undesired oligomers from the reaction medium, relative to corresponding oligomerization reactions carried out without such intervention. Such intervention in specific embodiments of the invention can include, for example, one or more of: addition of any agent or additive; removal of any reaction byproduct; and change of any reaction condition, whereby the oligomerization reactions takes place with reduced formation of undesired oligomers and/or reduced separation of the undesired oligomers from the reaction medium. Conventional techniques, such as templating and other pseudo-dilution techniques, while they may be additionally employed in the overall process of the present invention to maximize yield of desired macrocycle, form no part of modulation or modulating as contemplated by the present invention.

The phrase "byproducts" and "reaction byproducts" are used interchangeably herein to encompass any inorganic compounds, organic compounds, organometallic compounds, chemical elements, radicals, ions (cations/anions/Zwitterions), neutral particles, energized particles, or other applicable species that are produced by a specific reaction in the method of the present invention. Specifically, reaction steps that may produce byproducts include, but are not limited to, condensation reactions, oligomerization reactions, cyclization reaction(s), substitution reaction(s), metathesis reaction(s), etc.

The term "phase separation" as used herein broadly refers to separation of material from its surrounding environment due to physical and/or chemical differences between the material and its environment, or otherwise as a result of differences in properties between the material and its environment. Such term specifically covers, but is not limited to, the spontaneous separation of an insoluble or weakly soluble solid or gas from a liquid, or of an immiscible liquid from another liquid, or of a liquid or solid from a gas, due to a density differential therebetween. Such term, for example, encompasses any separation based on differences in size, shape, mass, density, solubility, volatility, permeability, diffusion rate, charge distribution, mass/charge ratio, binding affinity, adsorption/absorption potential, reactivity, or the like.

The term "phase transfer" as used herein broadly refers to transfer of material in a multi-phase environment (e.g., an environmental that contains two or more distinct, immiscible components as respect of phases), from one phase into another phase. The phases thus differ from one another in one or more physical and/or chemical characteristics, or in other differentiating properties. Such term specifically encompasses, but is not limited to, the transfer of one material from a first liquid component into a second liquid component that is distinct from and immiscible with such first liquid component. Such term further encompasses any transfer of material from one phase component to another based on differences in size, shape, mass, density, solubility, volatility, permeability, diffusion rate, charge distribution, mass/charge ratio, binding affinity, adsorption/absorption potential, and/or reactivity between such respective phase components.

The term "spontaneous" as used herein refers to a process that proceeds under internal force(s) and requires no external force(s) or intervention. A spontaneous process is not limited by any specific time frame, i.e., it may occur instantaneously or over a relatively long period of time.

BRIEF DESCRIPTION OF THE DRAWINGS

FIG. 4A shows a HPLC of the products produced by reaction of benzaldehyde and pyrrole in a solution containing 50% methanol and 50% water by volume.

FIG. 4B shows a HPLC of the products produced by reaction of benzaldehyde and pyrrole in a solution containing methanol and water at a volume ratio of 3:5 with about 0.014 g/ml NaCl.

DETAILED DESCRIPTION OF THE INVENTION

The contents of U.S. Provisional Patent Application No. 60/545,131 filed Feb. 17, 2004 in the names of Thomas E. Johnson and Billy T. Fowler for "METHODS AND COMPOSITIONS FOR FORMING CYCLIC COMPOUNDS" are incorporated herein by reference in their entirety for all purposes.

In general, synthesis of a macrocyclic compound involves cyclization of a linear precursor. The linear precursor can either be formed in situ from one or more starting materials, e.g., by oligomerization reaction, or the linear precursor be provided directly as the starting material for macrocyclic compound synthesis.

Figure 1A:
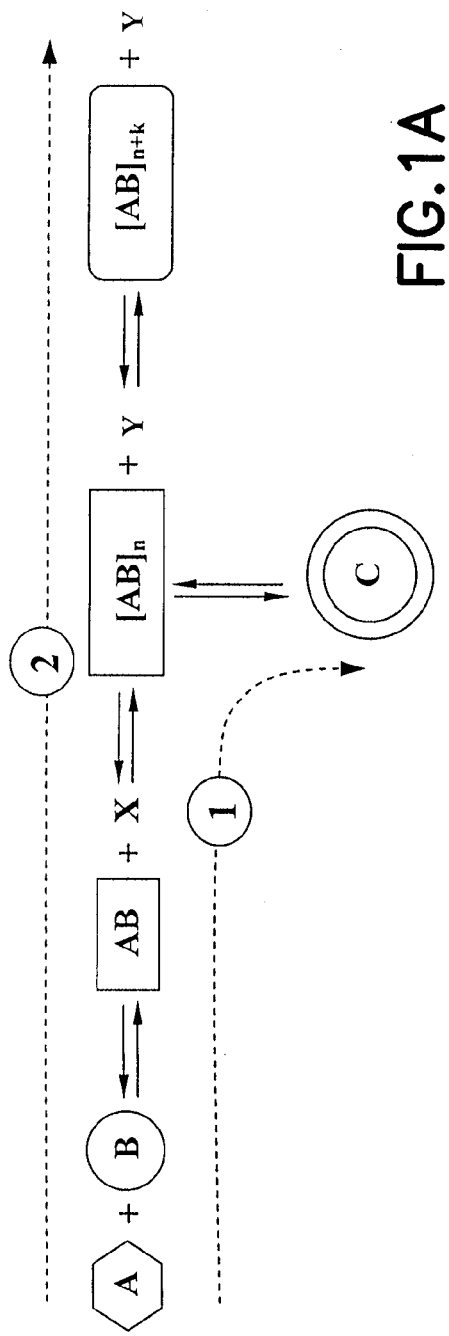
FIGS. 1A-1D illustrate a wide variety of generalized reaction processes for forming macrocyclic compounds.

FIG. 1A illustratively shows a process by which a macrocyclic compound C can be formed by oligomerization and cyclization reaction(s). Specifically, such process includes: (a) condensation reaction of two or more reactants A and B, forming a monomeric intermediate product AB; (b) reversible oligomerization of such monomeric intermediate product AB, forming a desired oligomer $[AB]_n$ of length n, and (c) reversible cyclization of such desired oligomer $[AB]_n$, forming the macrocyclic compound C. The oligomerization of AB that forms the desired oligomer $[AB]_n$ necessary for subsequent cyclization and formation of the compound C is the desired oligomerization. The condensation reaction, the desired oligomerization reaction and the cyclization reaction therefore define a desired reaction pathway 1 in which the reactants A and B form the macrocyclic compound C. Further, the desired oligomer $[AB]_n$ is susceptible to further, undesired oligomerization in forming undesired oligomers $[AB]_{n+k}$ of length (n+k). Such further oligomerization of the desired oligomer $[AB]_n$ defines an undesired reaction pathway 2, which directly competes with the desired reaction pathway 1 by reducing availability of the desired oligomer $[AB]_n$ for the cyclization reaction and causing significant reduction in the production yield of the macrocyclic compound C.

Figure 1B:
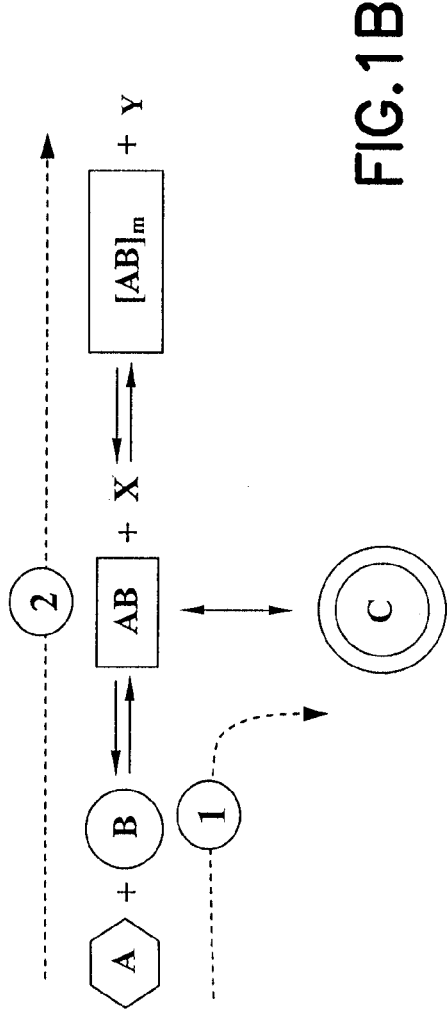

FIG. 1B illustratively shows another process for forming a macrocyclic compound C, which includes: (a) condensation reaction of two or more reactants A and B, forming a linear intermediate product AB; and (b) reversible cyclization of such linear intermediate product AB, forming the macrocyclic compound C. No oligomerization is required for formation of the macrocyclic compound C in this process. Instead, the condensation reaction and the cyclization reaction define the desired reaction pathway 1 in which the reactants A and B form the desired macrocyclic compound C. The linear intermediate product AB, however, is susceptible to undesired oligomerization in forming undesired oligomers $[AB]_m$ of length m. Such undesired oligomerization of the linear intermediate product therefore defines the undesired reaction pathway 2, which directly competes with the desired reaction pathway 1 by reducing availability of the linear intermediate product AB for the cyclization reaction and causing significant reduction in the production yield of the macrocyclic compound C.

Figure 1C:
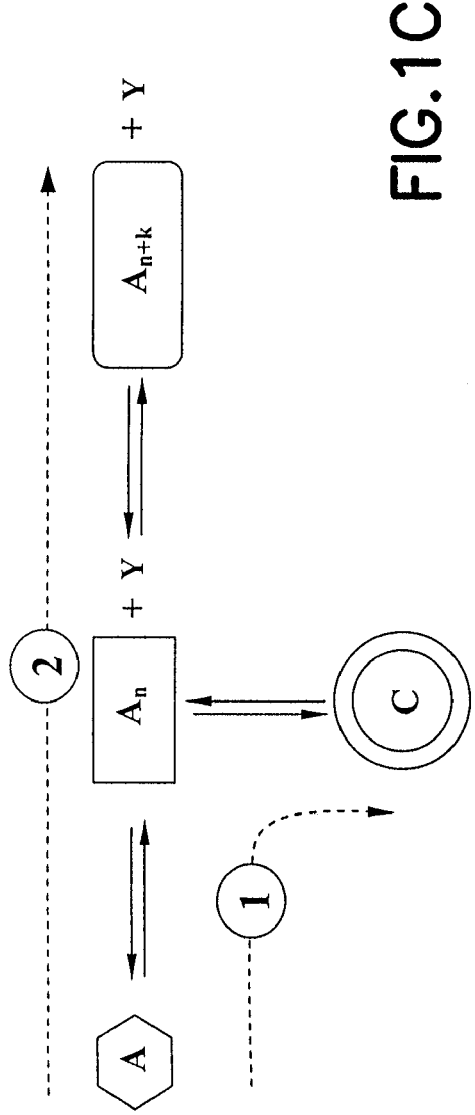

FIG. 1C illustratively shows a further process through which a macrocyclic compound C can be formed through oligomerization and cyclization. Specifically, such process includes: (a) reversible oligomerization of a single reactant A, forming desired oligomer $A_n$ of length n, and (b) reversible cyclization of such desired oligomer $A_n$, forming the macrocyclic compound C. The oligomerization of A that forms the desired oligomer $A_n$ necessary for subsequent cyclization and formation of the compound C is the desired oligomerization. The desired oligomerization reaction and the cyclization reaction therefore define the desired reaction pathway 1 in which the reactant A forms the desired macrocyclic compound C. In this reaction scheme, the desired oligomer $A_n$ is susceptible to further, undesired oligomerization in forming undesired oligomers $A_{n+k}$ of length (n+k). Such further, undesired oligomerization of the desired oligomer $A_n$ defines an undesired reaction pathway 2, which directly competes with the desired reaction pathway 1 by reducing availability of the desired oligomer $A_n$ for the cyclization reaction and causing significant reduction in the production yield of the macrocyclic compound C.

Figure 1D:
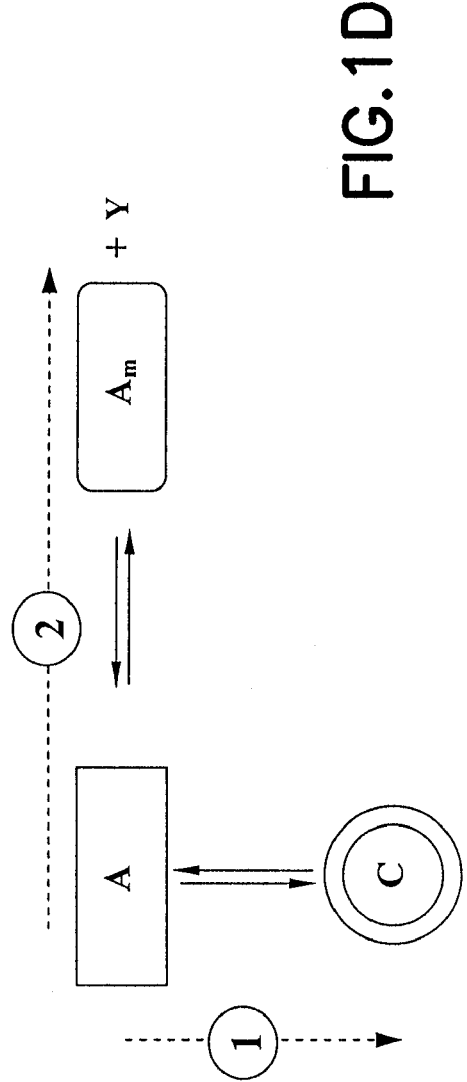

FIG. 1D illustratively shows another process for forming a macrocyclic compound C, which includes only reversible cyclization of a single reactant A, forming the macrocyclic compound C. No condensation or oligomerization is required for formation of the macrocyclic compound C in this process. Instead, the cyclization reaction alone defines the desired reaction pathway 1 in which the reactant A forms the desired macrocyclic compound C. The reactant A, however, is susceptible to undesired oligomerization in forming undesired oligomers $A_m$ of length m. Such undesired oligomerization of the reactant A therefore defines the undesired reaction pathway 2, which directly competes with the desired reaction pathway 1 by reducing availability of the reactant A for the cyclization reaction and causing significant reduction in the production yield of the macrocyclic compound C.

The reactants as mentioned hereinabove may contain any structure or functional groups, and they may include, but are not limited to, functional groups derived from methane, alkane primary, alkane secondary, alkane tertiary, cycloaliphatic ring, bicycloaliphatic ring, tricycloaliphatic ring, alkene, alkyne, monocyclic aromatic hydrocarbon, polycyclic aromatic hydrocarbon, biphenyl-type benzenoid ring, oxygen ether, thioether, S-heterocyclic ring, N-heterocyclic ring, saturated, N-heterocyclic ring, unsaturated, O-heterocyclic ring, epoxide, thioketone, alcohol, thiol, amine primary, amine secondary, amine tertiary, aldehyde, carboxylate ions, carboxylic acid, carboxylic acid ester, carboxylic thioester, dicarboxylic and tricarboxylic acids, amide, nitrile, oxime, thiocyanate, cyanamide, nitro, nitrate ester, diazo, organohalide, organomercurial, organoarsenical, organosilicon, organotin, organophosphate ester, thiophosphate ester, phosphonic acid, phosphinic acid, sulfonic acid, sulfate ester, peroxide, peracid, anhydride, alkaloids, grignard reagents, ketone acetals, ylides, keto esters, keto acids, N-acylamino acids, acychlorides, acylnitrenes, hydrazones, enamines, ketenes, thiophens, furans, pyrides, allyllic alcohol, aromatic nitrogen, aromatic alcohol, beta lactam fused, lactam, lactone, aromatic ketone, aromatic oxygen, oxime ether, urea, urethane, trihalide, cyclic ether, aryl halide, acetal ketal, sulfonamide, acyl halide, bismaleimides, alditols, aldotetroses, alkadienes, amidomalonic esters, alkatrienes, alkene oxides, alkenylbenzenes, alkyl halides, alkyl sulfates, alkyl tosylates, alkyl triflates, allenes, allylic halides, and amine oxides.

Although the above-described processes of FIGS. 1A-1D differ in the number of starting materials (i.e., reactants) and the specific reaction steps, they share the following common features:

(1) all processes form the macrocyclic compound C through cyclization of a linear precursor, e.g., the desired oligomer $[AB]_n$ in the process illustrated by FIG. 1A, the linear intermediate AB in the process illustrated by FIG. 1B, the desired oligomer $A_n$ in the process illustrated by FIG. 1C, and the reactant A in the process illustrated by FIG. 1D; and (2) such linear precursor is susceptible to undesired oligomerization in forming undesired oligomers, e.g., $[AB]_{n+k}$ in the process illustrated by FIG. 1A, $[AB]_m$ in the process illustrated by FIG. 1B, $A_{n+k}$ in the process illustrated by FIG. 1C, and $[A]_m$ in the process illustrated by FIG. 1D.

The undesired oligomerization reaction competes with the cyclization reaction, thus reducing the availability of the linear precursor for cyclization reaction and causing reduction in the production yield of the macrocyclic compound of interest. Moreover, when the undesired oligomers reach certain critical length, they may become insoluble or weakly soluble and will precipitate from the reaction medium or otherwise separate from the reaction medium, thereby converting the reversible oligomerization reaction into a virtually irreversible reaction that dominates over the cyclization reaction. In such event, the amount of undesired oligomers will far exceed the amount of macrocycles in the product mixture.

The present invention provides a solution to such problem, by modulating the oligomerization reaction, so as to reduce formation of the undesired oligomers and/or to reduce separation of the already-undesired oligomers from the reaction medium, relative to an unmodulated oligomerization reaction.

In one embodiment of the present invention, such oligomerization modulation is achieved by adding one or more oligomerization control additives into the reaction medium. Such oligomerization control additives can include any suitable materials whose addition affects the oligomerization reactions in such manner as to reduce formation of the undesired oligomers and/or separation of the already undesired oligomers from the reaction medium, relative to corresponding oligomerization reactions carried out without addition of such oligomerization control additives.

For example, for those oligomerization reactions in which an oligomerization byproduct is also formed in addition to the undesired oligomers, extraneous oligomerization byproduct can be added into the reaction medium to increase the overall oligomerization byproduct concentration in such reaction medium, thereby directing the reaction away from production of the undesired oligomers.

Figure 2:
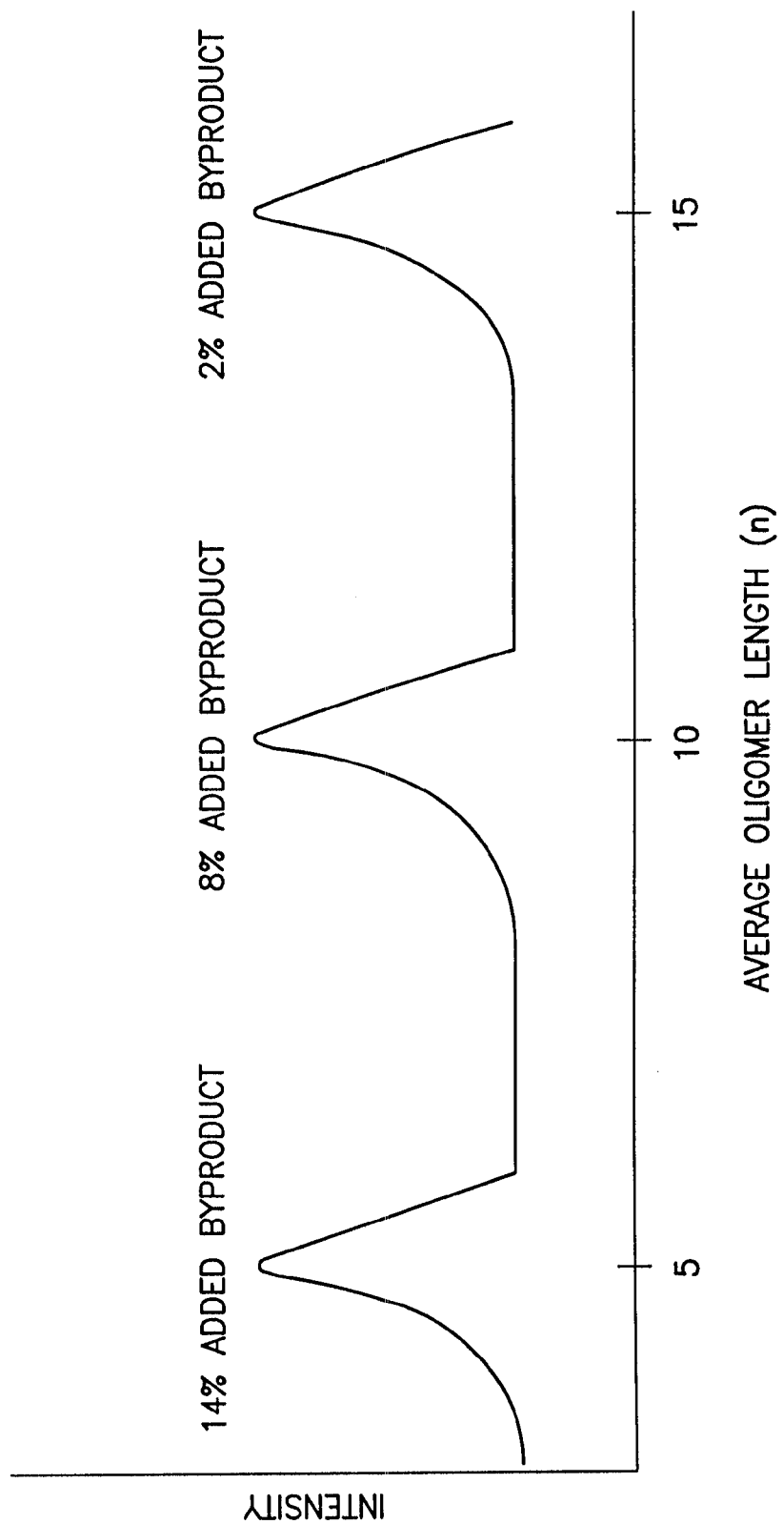
FIG. 2 is a graph of intensity as a function of average oligomer length, showing shifts in oligomer distributions when different concentrations of extraneous oligomerization byproduct are introduced to the reaction system.

More importantly, the overall oligomerization byproduct concentration in the reaction medium can be adjusted to provide a product distribution of desired oligomers of selected lengths. In general, the higher the oligomerization byproduct concentration, the shorter the average length of the oligomers formed in the reaction medium. FIG. 2 illustrates the shift in oligomer distributions, when different amounts of extraneous oligomerization byproduct are added. For example, when 14% extraneous oligomerization byproduct (based on the total volume of the reaction medium) is added, the distribution of the average oligomer length peaks at about 5, which means that the oligomerization reaction as thus modulated favors formation of pentamers. As another example, when 8% (by volume) extraneous oligomerization byproduct is added, the peak of the average oligomer length distribution shifts to about 10, which means that the modulated oligomerization reaction now favors formation of longer oligomers of about length 10. As a still further example, when only 2% (by volume) extraneous oligomerization byproduct is added, the peak of the average oligomer length distribution further shifts to about 15, which means that the modulated oligomerization reaction now favors formation of oligomers of about length 15.

Therefore, by adjusting the amount of added extraneous oligomerization byproduct, the extent of the oligomerization reaction can be controlled to favor formation of the desired oligomers of a specific length (n) for cyclization to form the macrocyclic compound.

The extraneous oligomerization byproduct used for modulating the oligomerization reaction is selected based on the specific oligomerization reaction involved. For example, suitable extraneous oligomerization byproducts that can be used in specific instances within the broad scope of the present invention include, but are not limited to, adenosine 5'-monophosphate (AMP), cytidine 5'-monophosphate (CMP), guanosine 5'-monophosphate (GMP), thymidine 5'-monophosphate (TMP), uridine 5'-monophosphate (UMP), adenosine di-phosphate (ADP), cytidine di-phosphate (CDP), guanosine di-phosphate (GDP), thymidine di-phosphate (TDP), uridine di-phosphate (UDP), pyrophosphoric acid, alkyl pyrophosphates, pyridine, aniline, benzyl alcohol, water, dihydrogen sulfide, methanol, ethanol, propanol, butanol, bromide, alkylthiol, thiophenol, 2-butyne, acetic acid, acetone, carbon dioxide, carbon monoxide, deuterium oxide, fructose, galactose, gallic acid, glycerol, glucose, hydrochloric acid, hydrogen cyanide, hydrobromic acid, hydroiodic acid, iodoform, lactic acid, nitrogen, nitrous acid, ammonia, methyl amine, ethyl amine, propyl amine, butyl amine, dimethyl amine, diethyl amine, dipropyl amine, trimethyl amine, triethyl amine, hydrogen, phenol, sulfur dioxide, phosphoric acid, ethylene, sulfuric acid, silanes, silylethers, sulfonic acids, sulfite esters, sulfenic acids, sulfinic acids, disulfides, peroxides, boronic acids, borate ethers, triflates, mesylates, sulfates, alkyl halides, perchloric acid, periodic acid, sulfones, sulfoxides, succinimide, N,N-diisopropylurea, amino acids, methyl thiocyanate, and N-hydroxysuccinimide.

For those oligomerization reactions in which the undesired oligomers formed are insoluble or weakly soluble in the reaction medium, oligomerization modulation can be achieved by providing an oligomerization control additive that includes one or more solubilizing functional groups and functions as a solubilizing agent. One or more oligomerization additives can be employed, as necessary or desirable, in a specific application of the methodology of the invention. The solubilizing agent participates in the undesired oligomerization reaction to form modified undesired oligomers that incorporate the solubilizing functional group(s). Such modified undesired oligomers, due to incorporation of the solubilizing functional group(s) therein, become more soluble in the reaction medium and less susceptible to separation therefrom. In this manner, the undesired oligomers are kept in the reaction medium and may be reversibly converted to the desired oligomers or other linear precursors for the cyclization reaction.

Further, the oligomerization control additive may include a compound or solvent species that interacts with the reactants or one or more intermediate products of such reactants to affect the oligomerization reactions in such a manner that formation of the undesired oligomers is reduced.

In addition to the use of oligomerization control additives as described hereinabove, oligomerization modulation within the broad practice of the present invention may further include removal of one or more reaction byproducts, to affect the oligomerization reactions so that formation of the undesired oligomers is reduced, and/or formation of the desired oligomer is favored, relative to a corresponding reaction scheme lacking such byproduct removal.

Oligomerization modulation can also be achieved by changing the reaction conditions in such a manner that the reaction equilibria change to favor the desired reaction pathway over the reaction pathway yielding undesired oligomers, thereby forming more macrocyclic compound instead of undesired oligomers. For example, by change of reaction temperature, pressure, pH value, energetic state, magnetic state, and/or photonic state, the equilibria of the oligomerization and cyclization reaction(s) can be changed to stimulate formation of the macrocyclic compound and suppress formation of the undesired oligomers. Such techniques can be used either in conjunction with, or independent of, the use of oligomerization control additives.

Modulation of the oligomerization reaction according to the present invention can be used to effectively minimize or other significantly reduce the impact of the undesired oligomerization, and thereby achieve significantly increased yield of the macrocyclic compound.

In certain reaction systems, multiple macrocyclic compounds of different sizes can be formed via different reaction pathways that include cyclization reaction(s) of different oligomers. Suitable oligomerization modulation techniques can therefore be selected to reduce formation of the undesired oligomers, thereby reducing formation of those macrocyclic compounds that are undesired and achieving improved product distribution that favors the formation of one or more macrocyclic compound(s) of desired size(s).

Macrocyclic compounds formed by the cyclization reaction(s) under the influence of the above-mentioned oligomerization modulation process can be recovered by any suitable methods or techniques now known or hereinafter discovered in the art. Preferably, such macrocyclic compound is selectively separated from the reaction medium, based on differences in one or more physical and/or chemical characteristics, or other material properties, between such macrocyclic compound and other components of the reaction medium.

For example, the macrocyclic compound can be selectively separated from the reaction medium based on permeability difference therebetween, by passing the reaction medium through a semi-permeable membrane that is selectively permeable to such macrocyclic compound but is impermeable to the starting materials, the desired/undesired oligomers, and other components of the reaction medium, or which, alternatively, is impermeable to the macrocyclic compound but is permeable to all other components of the reaction medium. As another example, the macrocyclic compound can be selectively separated from the reaction medium based on affinity difference therebetween, by passing the reaction medium through an affinity column that has selective binding affinity for the macrocyclic compound but not for the other components of the reaction medium. As a further example, the macrocyclic compound can be selectively separated from the reaction medium by application of an electric field, if such macrocyclic compound carries a charge that is different from those carried by the other components of the reaction medium. As a still further example, the macrocyclic compound can be selectively separated from the reaction medium by application of a magnetic field, if the macrocyclic compound exhibits a different magnetic state from those of the other components of the reaction medium.

The physical and/or chemical characteristic differences that can be used for separating the macrocyclic compound from the reaction medium include, but are not limited to, differences in size, shape, mass, density, solubility, volatility, permeability, diffusion rate, charge distribution, mass/charge ratio, binding affinity, adsorption/absorption potential, reactivity (e.g., metal coordination, electrostatic interactions, hydrogen bonding, donor-acceptor interactions, and covalent bond formation), etc., which have been widely used in a wide variety of well-known separation methods, such as filtration, evaporation, flash expansion, distillation, stripping, absorption, extraction, crystallization, adsorption, ion exchanging, drying, leaching, washing, clathration, osmosis, reverse osmosis, bubble fractionation, magnetic separation, chromatography, freeze drying, condensation, gel filtration, gaseous diffusion, sweep diffusion, thermal diffusion, mass spectrometry, dialysis, electrodialysis, electrophoresis, ultra-centrifugation, ultra-filtration, molecular distillation, demisting, settling, centrifugation, cyclone flow separation, electrostatic precipitation, etc.

It is to be emphasized that the above-listed physical and chemical characteristic differences and separation techniques are only illustrative of some of the vast numbers of separation characteristics and techniques that can be usefully employed in the broad practice of the present invention. Accordingly, the foregoing should not be construed as an exhaustive listing and should not be interpreted in any manner as limiting the broad scope of applicability of the present invention.

In a preferred embodiment of the present invention, the reaction medium composition and the reaction conditions are adjusted so that the macrocyclic compound formed by the cyclization reaction spontaneously separates from the reaction medium via phase separation or phase transfer, without requirement for external force or energy.

For example, when the reaction medium is in a liquid phase, the reaction medium composition and the reaction conditions can be selected to form the macrocyclic compound as a solid that is insoluble or weakly soluble in such reaction medium, so that such macrocyclic compound precipitates out of the reaction medium upon formation. Such macrocyclic compound can alternatively be a liquid phase material that is immiscible or weakly miscible in the reaction medium, so that it spontaneously separates into a different liquid layer, e.g., on top of or underneath the reaction medium layer, depending on its specific gravity characteristics. Such macrocyclic compound as a further alternative can be a gaseous product that is insoluble or weakly soluble in said reaction medium, so that it spontaneously bubbles out of the reaction medium upon formation. As yet another alternative, the reaction medium can be provided in a gaseous state, in which the macrocyclic compound is formed as a liquid or alternatively a solid that spontaneously separates from the gaseous reaction medium by condensation or solidification, respectively.

Multiphase reaction systems can also be employed in the present invention to achieve spontaneous separation of the macrocyclic compound via phase transfer. For example, the reaction medium can be provided as a first liquid phase component of a multiphase reaction system, while a second liquid phase component immiscible or weakly immiscible in such reaction medium is provided as a liquid layer or volume adjacent to the reaction medium. The macrocyclic compound to be formed is insoluble or weakly soluble in the first liquid phase component defined by the reaction medium but is soluble or moderately soluble in the second liquid phase component. Therefore, macrocyclic compound that forms in the reaction medium and contacts the liquid-liquid interface of these two liquid phase components will spontaneously transfer from the reaction medium into the adjacent second liquid phase component, thereby separating from the reaction medium.

The spontaneous separation of the macrocyclic compound as described hereinabove advantageously provides a driving force that continuously drives the cyclization reaction toward the macrocyclic compound, and such mode of reaction and separation therefore is a particularly preferred approach in the practice of the present invention.

The spontaneous separation of the macrocyclic compound from the reaction medium can be effectuated by selecting suitable solvents and/or additives, and/or by adjusting the reaction conditions, to maximize the production of the macrocyclic compound. Preferably, the composition of the reaction medium and the reaction conditions are adjusted so that the reactants and at least the desired oligomers are soluble in such reaction medium, and the macrocyclic compound is insoluble or only weakly soluble in the reaction medium, thereby selectively separating the macrocyclic compound from the reaction medium.

In one specific embodiment of the present invention, the reaction medium comprises a single solvent for dissolving the reactants and selectively separating the macrocyclic component.

In an alternative embodiment, a reacting solvent and a co-solvent are provided in the reaction medium, with the reacting solvent functioning to dissolve the reactants, and the co-solvent functioning to effectuate spontaneous separation of the macrocyclic compound from the reaction medium. Preferably, such reacting solvent and co-solvent operate to define a reaction medium in which the reactants and the desired oligomers are soluble, and the macrocyclic compound is insoluble or only weakly soluble.

As mentioned hereinabove, when the undesired oligomers reach certain lengths, they may become insoluble or only weakly soluble in the reaction medium and start to precipitate out of the reaction medium. Such problem can be effectively dealt with by employing suitable oligomerization control techniques as described hereinabove to reduce formation of such undesired oligomers and/or reduce separation of the undesired oligomers from the reaction medium.

Suitable co-solvents that can be used in the broad practice of the present invention for effectuating spontaneous separation of the macrocyclic compound from the reaction medium include, but are not limited to, water, methanol, ethanol, isopropanol, tert-butanol, n-propanol, iso-butanol, n-butanol, ethylene glycol, propylene glycol, formic acid, limonene, dipropylene glycol, monomethyl ether, diethylene glycol, ethyl ether, tripropylene glycol, monomethyl ether, dimethyl sulfoxide, phenol, polypropylene glycol, N-methyl-2-pyrrolidone, acetone, ethyl acetate, glycolfurol, solketal, glycerol, formol, formamide, nitrobenzene, tetrahydrofuryl alcohol, polyethylene glycol, dimethyl isosorbide, dimethyl acetamide, methyl ethyl ketone, 1,4-dioxane, hydrosols, acetonitrile, ammonia, methyl amine, ethyl amine, propyl amine, butyl amine, dimethyl amine, diethyl amine, dipropyl amine, trimethyl amine, triethyl amine, dimethylformamide, tetrahydrofuran, glycol ethers, methyl cellosolve, cellosolve, butyl cellosolve, hexyl cellosolve, methyl carbitol, carbitol, butyl carbitol, hexyl carbitol, propasol solvent B, propasol solvent P, propasol solvent M, propasol solvent DM, methoxytriglycol, ethoxytriglycol, butoxytriglycol, 1-butoxyethoxy-2-propanol, phenyl glycol ether, glymes, monoglyme, ethylglyme, diglyme, ethyl diglyme, triglyme, butyl diglyme, tetraglyme, aminoalcohols, sulfolane, hexamethylphosphorictriamide (HMPA), nitromethane, methyl ethylether, carbon disulfide, methale chloride, chloroform, tetrahydrofuran, toluene, and benzene.

In addition to, or independent of, such co-solvent, one or more separation additives can be provided in the reaction medium for effectuating spontaneous separation of the macrocyclic compound from the reaction medium.

For example, such separation additives may encompass salts with cations selected from the group consisting of aluminum, ammonium, barium, calcium, chromium(II), chromous, chromium(III), chromic, copper(I), cuprous, copper (II), cupric, iron(II), ferrous, iron(III), ferric hydrogen, hydronium, lead(II), lithium, magnesium, manganese(II), manganous manganese(III), manganic, mercury(I), mercurous, mercury(II), mercuric, nitronium, potassium, silver, sodium, strontium, tin(II), stannous, tin(IV), stannic, zinc oxonium, sulfonium, selenonium, chloronium, bromonium, iodonium, tetramethylammonium, dimethyloxonium, diphenyliodonium, ethylenebromonium, anilinium, guanidinium, 2-phenylhydrazinium, 1-methylhydrazinium, acetohydrazidium, benzamidium, acetonium, 1,4-dioxanium, ethylium or ethenium, phenylium, 2-cyclohexen-1-ylium, 9-anthrylium, neopentylium, triphenylmethylium or triphenylcarbenium, methanediylium, cyclopropenylium, ethane-1,1-diylium, ethane-1,2-diylium, acetylium, methylsulfanylium or methanesulfenylium, methanesulfonylium, benzylideneaminylium, quinolizinyum, 1,2,3-benzodithiazolylium, methyliumyl, ethan-2-ium-1-yl, 3-methyl-1-(trimethylsilyl)triaz-2-en-2-ium-1-id-2yl, 1,2,2,2-tetramethyldiazan-2-ium-1-ide, azanylium, aminylium, nitrenium, phenylsulfanylium, tetramethyl-λ$^5$-phosphanylium, tetramethylphosphoranylium, tetramethylphosphonium, 3-methyltriaz-1-en-1-ylium, heptamethyltrisilan-2-ylium, 4-cyclopropyltetrasulfan-1-ylium, cyclooct-3-en-1-ylium, furan-2-ylium, 1,2-bis(4-methoxyphenyl)-2-phenylethen-1-ylium, bicyclo[2.2.1]heptan-2-ylium, spiro[4.5]decan-8-ylium, propane-1,3-bis(ylium), 2,2-dimethyldiazane-1,1-bis(ylium), 2,2-dimethylhydrazine-1,1-bis(ylium), propane-2,2-bis (ylium) 1-methylethane-1,1-bis(ylium), cyclobut-3-ene-1,2-bis(ylium), propane-1,2,3-tris(ylium), ammonium, methanediazonium, methyldiazenylium, benzothiazole-2-diazonium, benzothiazol-2-yldiazenylium, 2,4-dioxopentane-3-diazonium, (2,4-dioxopentan-3-yl) diazenylium, (1-acetyl-2-oxopropyl)diazenylium, benzene-1,4-bis(diazonium), 1,4-phenylenebis(diazenylium), 3,5-dimethyl-1,4-dihydropyridin-1-ylium, 3,5-dimethylpyridin-1(4h)-ylium, acetylium, hexanethioylium, cyclohexanecarbonylium, ethenesulfonylium, dimethylphosphinoylium, methylphosphonoylium, glutarylium, pentanedioylium, pyridine-2,6-dicarbony.

Such separation additives may further encompass salts including anions selected from the group consisting of hydride, oxide, fluoride, sulfide, chloride, nitride, bromide, iodide, nitrate, nitrite, chromate, chlorate, chlorite, dichromate, sulfate, sulfite, phosphate, phosphite, carbonate, acetate, hydroxide, cyanate, cyanide, hydrogen sulfate, hydrogen sulfite, hydrogen carbonate, hydrogen phosphate, hypochlorite, dihydrogen phosphate, perchlorate, oxalate, permanganate, silicate, thiocyanate, iodate, Bromate, hypobromate, formate, amide, hydroxide, peroxide, oxide, oxalate, arsenate, arsenite, hydride, fluoride, chloride, bromide, iodide, sulfide, nitride, Hexanoate, cyclohexanecarboxalyte, benzenesulfate, 1-butanide, 1-butyn-1-ide, benzenide, triphenylmethanide, diphenylmethanediide, cyclopentadienide, 1,4-dihydro-1,4-naphthalenediide, Ethylide or ethene anion, Dihydronaphthylide or naphthalene anion, p-benzosemiquinone anion, methanide, but-1-yn-1-ide, propan-2-ide, diphenylmethanediide, tetramethylboranuide, benzenesulfonate, dibenzylphosphinite, methanolate, benzene-1,4-bis(thiolate), cyclohexaneselenolate, 3-hydroxybenzene-1,2-bis(olate), carboxylato, phosphonato, sulfonato, oxido, methanidyl, amidylidene, disulfanidyl, phosphanida, boranuida, methyl anion, acetyl anion, phenyl anion, benzenesulfinyl anion, methanaminyl anion, methylazanyl anion, cyclopenta-2,4-dien-1-yl anion, diphenylmethylene dianion, 1,4-dihydronaphthalene-1,4-diyl dianion, methylamide, methylazanide, dimethylphosphanide, dimethylphosphinide, tributylstannanide, methylidynesilanide, (diphenylboryl)methanide, tricyanomethanide, propan-2-ide, but-1-yn-1-ide, 1,3-diphenylprop-2-en-1-ide1, 1,2-tricyano-2-(3,4-dicyano-5-imino-1,5-dihydro-2H-pyrrol-2-ylidene)ethan-1-ide, 4-chlorobenzen-1-ide, cyclopenta-2,4-dien-1-ide, 7bH-indeno[1,2,3-jk]fluoren-7b-ide, 1,5-di-p-tolylpentaaza-1,4-dien-3-ide, 1H-benzotriazol-1-ide, $C_6H_5$—$N^2$-phenylimide, diphenylmethanediide, 9H-fluorene-9,9-diide, 1,4-dihydronaphthalene-1,4-diide, 1,1,1,5,5,5-hexamethyltrisilazane-2,4-diide, 1,3-diphenylpropane-1,2,3-triide, 1,4,6,9-tetrahydropyrene-1,4,6,9-tetraide.

Preferably, such salts comprise an anion such as $F^-$, $Cl^-$, $Br^-$, $I^-$, $SO_4^{2-}$, $HSO_4^-$, $Ph_4B^-$, $NO_3^-$, $SO_3^{2-}$, and $BO_2^-$ or a cation such as ammonium, copper (II), iron (III), magnesium, potassium, sodium, zinc, guanidinium, triphenylmethylium, and tetramethylphosphonium.

Such salts can interact with the solvents contained in the reaction medium, and/or interact with the macrocyclic compound, in such a manner that the macrocyclic compound becomes less soluble in such reaction medium and spontaneously separates from the reaction medium upon its formation. Further, such salts may interact with the other components of the reaction medium to reduce separation of such components from the reaction medium.

By selecting the appropriate oligomerization control additive(s), reacting solvent(s), co-solvent(s), and/or separation additive(s), one can readily adjust the product distribution of the oligomerization and/or cyclization reactions and improve the production yield of the macrocyclic compound.

Figure 3:
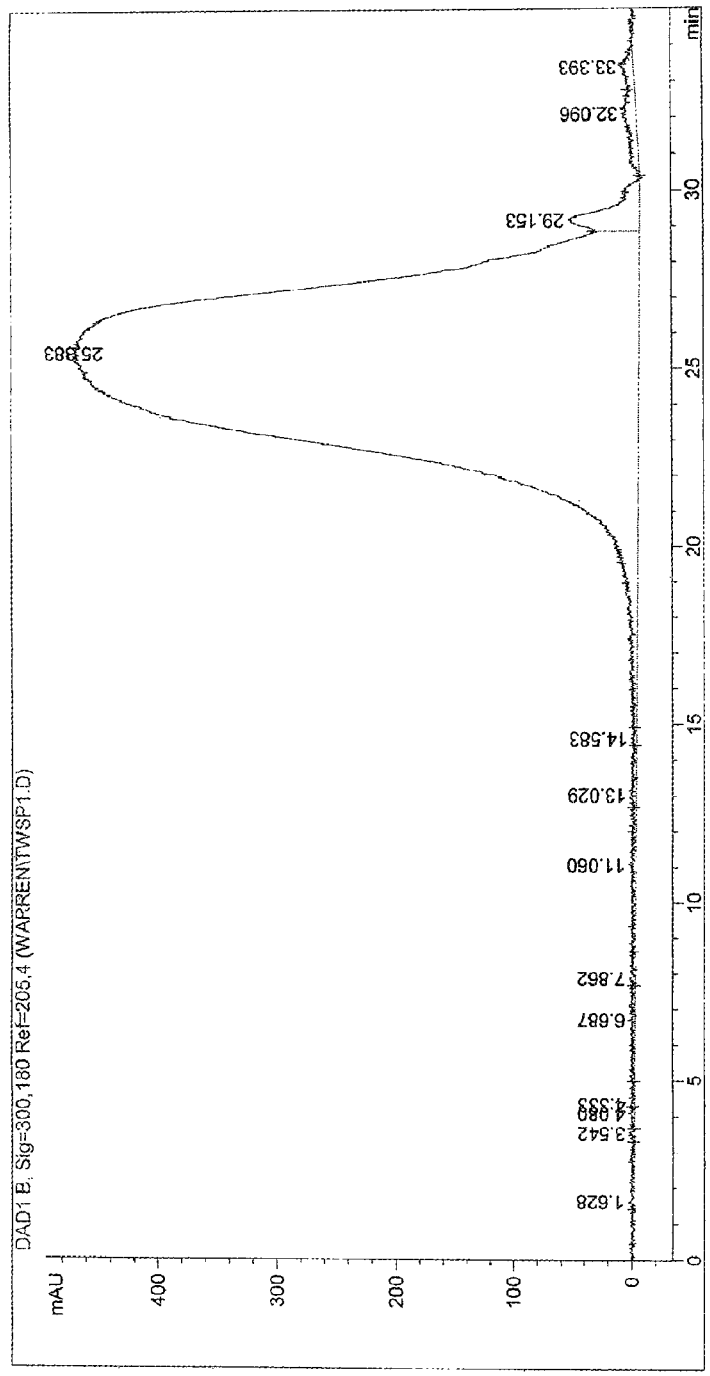
FIG. 3 shows a high-performance liquid chromatograph (HPLC) of the products produced by reaction of benzaldehyde and pyrrole in an absolute ethanol solution without oligomerization control.

For example, FIG. 3 is a HPLC chromatograph for the products formed by reacting benzaldehyde and pyrrole (which are used to form tetraphenylporphyrinogen) in absolute ethanol (which functions as a precipitating solvent for selectively precipitating the non-polar tetraphenylporphyrinogen so formed), without any oligomerization control. The lack of oligomerization control in such reaction results in formation of a wide variety of reaction products, as indicated by the Gaussian distribution. Majority of such reaction products were linear extended oligomers that were formed and precipitated out of the reaction solution concurrently with the tetraphenylporphyrinogen, with only a small amount of tetraphenylporphyrinogen (as represented by the peak at 29.153), approximately less than 1%.

Figure 4A:
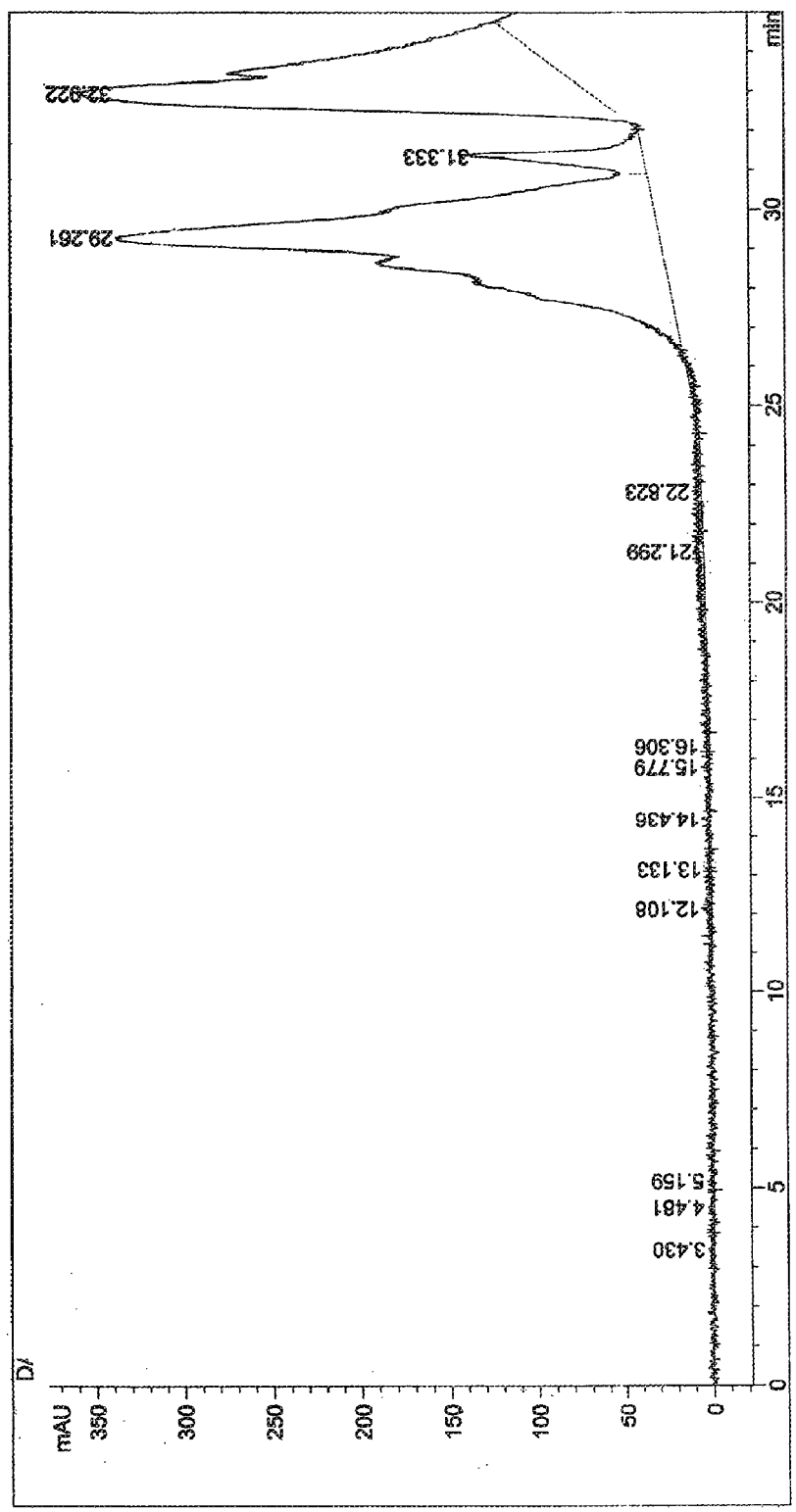
FIGS. 4A and 4B show HPLC chromatographs of the products produced by reaction of benzaldehyde and pyrrole in solutions containing precipitating solvent and oligomerization control additive species.
Figure 4B:
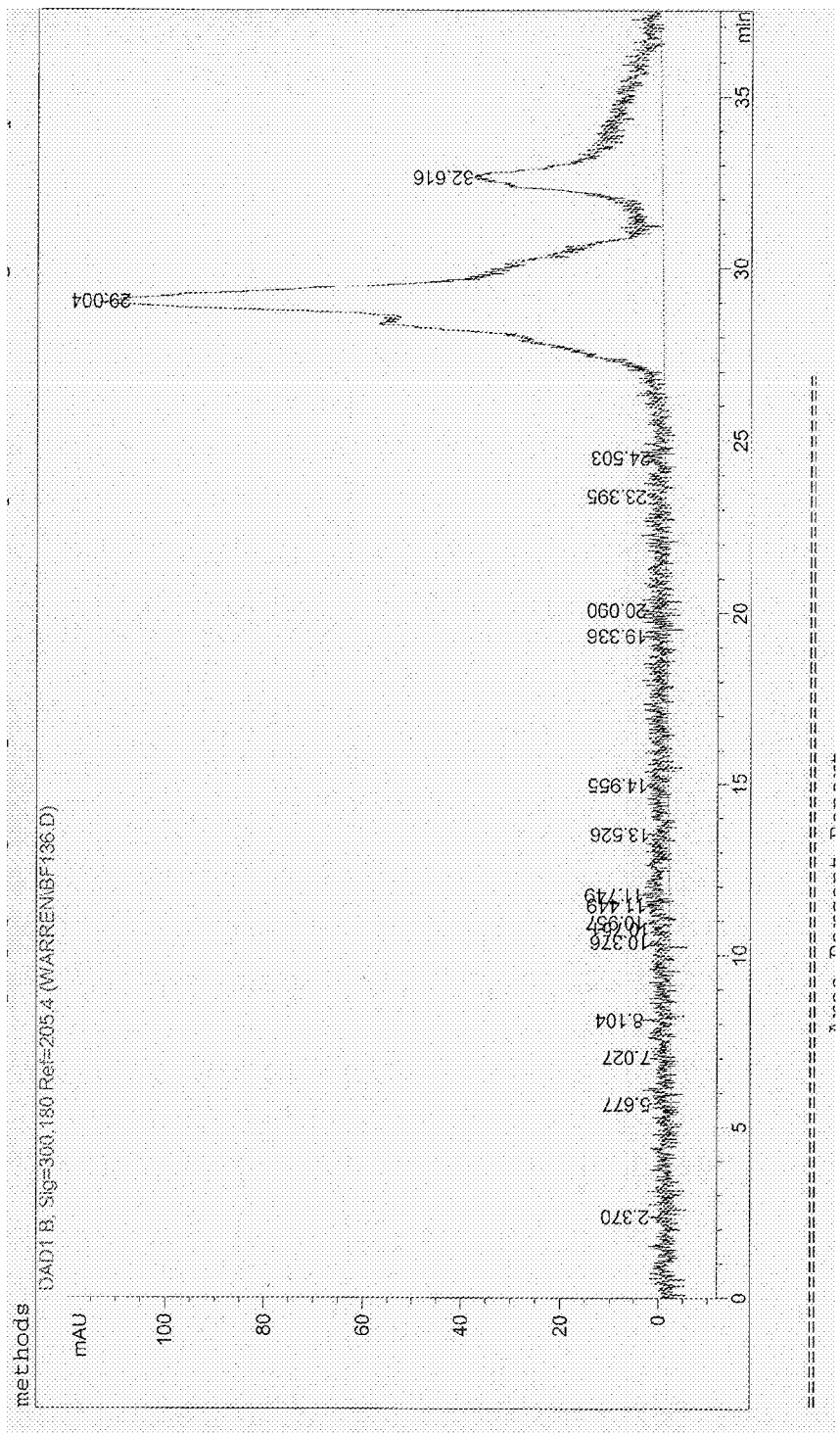

By reacting benzaldehyde and pyrrole in a reaction composition that comprises ethanol (i.e., the precipitating solvent) and water (i.e., the oligomerization control additive) at a volumetric ratio of 1:1, approximately 30% of the reaction products were tetraphenylporphyrinogen, as mixed with undesired oligomers. FIG. 4A is a HPLC chromatograph for the products formed by reacting benzaldehyde and pyrrole in a reaction composition that comprises methanol (i.e., a different precipitating solvent) and water (i.e., the oligomerization control additive) at a volumetric ratio of 1:1. About 75% of the reaction products were tetraphenylporphyrinogen (as represented by the peak at 29.261). FIG. 4B is a HPLC chromatograph for the products formed by reacting benzaldehyde and pyrrole in a reaction composition that contained about 37.5% by volume of methanol (i.e., the precipitating solvent), 62.5% by volume of water (i.e., the oligomerization control additive), and 0.014 g/ml of NaCl (i.e., the separation additive). The reaction composition used in FIG. 4C contained a higher concentration of oligomerization control additive for more effective modulation of the oligomerization reactions, and the separation additive NaCl functioned to further adjust the solvent strength of the reaction composition for more selective separation of the macrocyclic compound. Consequently, the production yield of the tetraphenylporphyrinogen (as represented by the peak at 29.004) was further improved to about 85%. Addition of water in the synthesis of non-polar porphyrinogens is completely opposite to the teachings of the conventional wisdom, which advocates removal of water instead, and it surprisingly and unexpectedly improves the production yield of the non-polar porphyrinogen (e.g., tetraphenylporphyrinogen) by almost a hundred fold.

In another embodiment of the present invention, a solid-phase substrate can be employed for immobilizing at least one of the reactants and facilitating solid-phase reactions, to thereby form a macrocyclic compound that is also immobilized on such solid-phase substrate. In this circumstance, separation of the macrocyclic compound can be carried out by removing the solid-phase substrate from the reaction medium and subsequently releasing the immobilized macrocyclic compound from such substrate. Such solid-phase substrate technique is amenable to automation, and it is particularly suitable for producing libraries of macrocycles in the practice of the method of the present invention.

As mentioned hereinabove, in a thermodynamically controlled, reversible reaction, the relative stabilities of all products, macrocyclic or acyclic, determine the product distribution. Therefore, the reaction medium of the present invention may further comprise a stabilizing agent that selectively stabilizes the macrocyclic compound, so as to increase the relative proportion of the macrocyclic compound in the reaction end product mixture. Such stabilizing agent can be of any suitable type, as for example including, organic, inorganic, or organometallic compounds, ions, or chemical elements. Preferably, the stabilizing agent is a salt with metallic or inorganic ions that bind to the macrocyclic compound and form a more stable complex than the macrocyclic compound. Alternatively, the macrocyclic compound itself can be engineered to undergo intramolecular rearrangement after the ring closure reaction, thereby forming a different macrocyclic form that is more stable than the original macrocyclic compound. Further, an electric and/or magnetic field can be applied to the reaction composition for selectively stabilizing the macrocyclic compound.

The reaction medium of the present invention may further comprise a cyclization agent that facilitates the ring closure or cyclization reaction(s). For example, such cyclization agent can include a template material, which pre-organizes the reactive ends of the desired oligomers for more effective cyclization. A template material, as mentioned hereinabove, can be employed to complementarily bind to a cavity formed by the macrocyclic compound and to form a more stable complex with such macrocyclic compound. In such manner, the template material functions both as a cyclization agent and a stabilizing agent. As another example, the cyclization agent can include a material with microporous structure, such as Smectite clay, which provides a localized environment that is highly favorable to the ring closure reaction. Further, the cyclization agent can include certain structural elements that function to bend the linear structures of the desired oligomers and form pre-organized ring structures, as discussed hereinabove.

The reaction medium in the practice of the present invention can further include any suitable catalyst materials now or hereafter discovered for catalyzing one or more reactions in the reaction medium.

The methodology of the present invention can also be used to synthesize a macrocyclic compound of interest, by first forming a macrocyclic intermediate compound through a desired reaction pathway involving at least cyclization reaction(s) as described hereinabove, and then modifying such macrocyclic intermediate compound to form the macrocyclic compound of interest. The modification of the macrocyclic intermediate compound may comprise one or more steps such as oxidation, reduction, substitution of at least one functional group, removal of at least one functional group, addition of at least one functional group, further cyclization, isomeric rearrangement, and/or purification. Such modification can be carried out either in situ in the same reaction medium as employed for the cyclization reaction(s), without separation of the macrocyclic compound, or subsequently in a different reaction medium, by first separating the macrocyclic compound from the cyclization reaction medium.

The present invention in a further aspect provides a system for manufacturing a macrocyclic compound, which may be employed to carry out the synthesis methodology of the invention in a highly effective manner.

Figure 20:
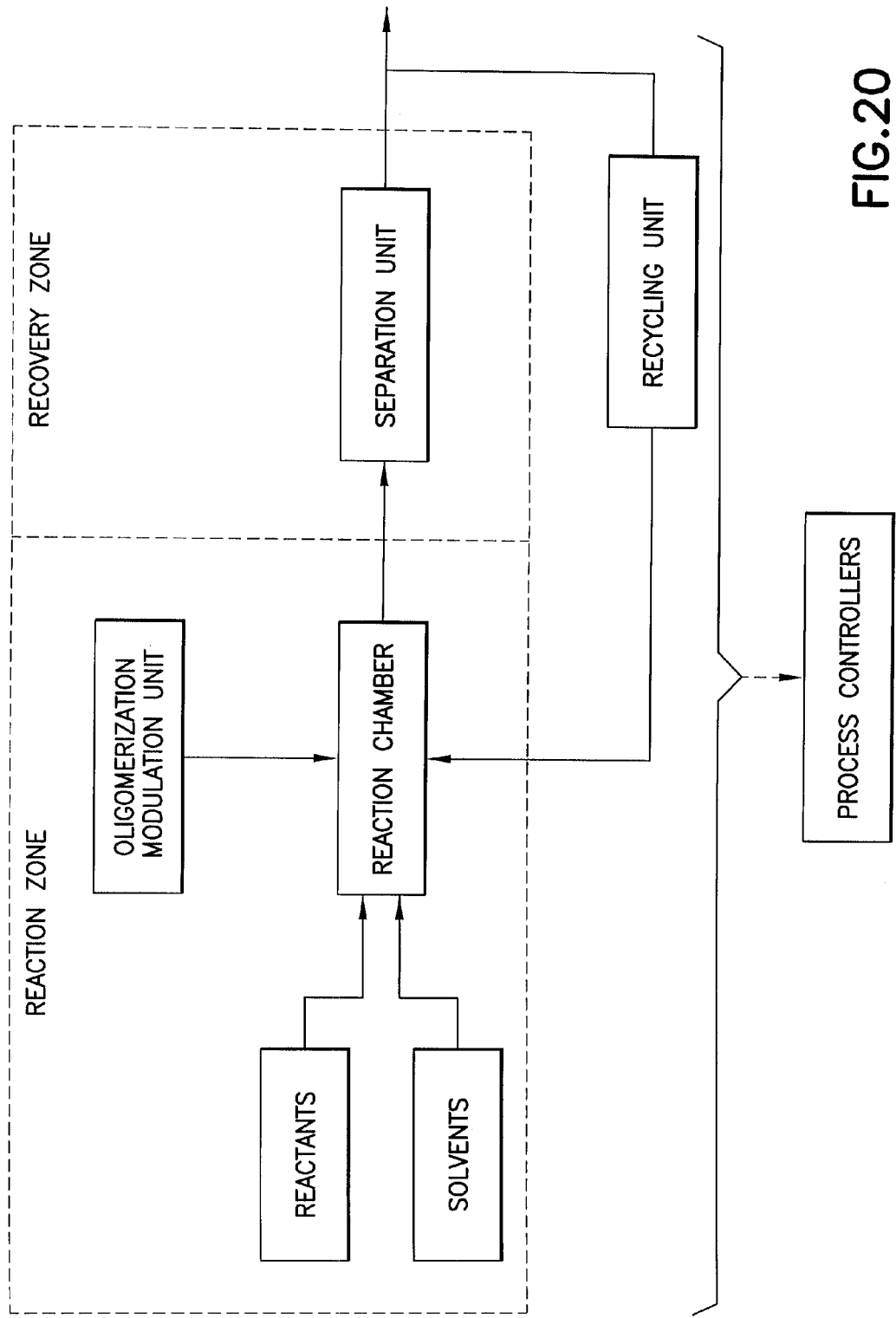
FIG. 20 is a schematic representation of a system for manufacturing macrocyclic compounds, according to one embodiment of the present invention.

FIG. 20 shows a schematic representation of one such system, which includes a reaction zone having: (1) one or more supply vessels for supplying one or more reactants and/or one or more solvents that are needed for forming the macrocyclic compound, (2) a reaction chamber coupled with such supply vessels for receiving the reactants and solvents and effectuating reactions of the reactants therein to form the macrocyclic compound, and (3) an oligomerization modulation unit for modulating oligomerization reactions of the reactants in the reaction chamber, so as to reduce formation of undesired oligomers by the reactants and/or to reduce separation of the undesired oligomers from the reaction medium, relative to corresponding unmodulated oligomerization reactions.

The reaction chamber may include one or more reactors of suitable type(s), as for example selected from among: continuous reactors, batch reactors, fixed-bed reactors, fluidized-bed reactors, bubbling fluid reactors, circulating fluid bed reactors, slurry-phase reactors, packed-bed reactors, trickle-bed reactors, multi-tubular fixed-bed reactors, quench reactors, double-wall heat-exchanging reactors, radial flow reactors, plug flow reactors, continually stirred tank reactors, semi-batch reactors, semi-continuous reactors, bypass reactors, differential reactors, swing reactors, continuous regeneration reactors, multi-stage reactors, and membrane-based reactors. The reaction chamber may include a single reactor in which all the reactions are carried out, or multiple reactors arranged in parallel or in series for carrying out multiple processes.

The oligomerization modulation unit may include one or more additive supply vessels for adding one or more oligomerization control additives to the reaction chamber, or it may include one or more process controllers for changing the reaction conditions in the reaction chamber, consistent with the description hereinabove.

Further, such reaction system of the present invention can include a recovery zone, either downstream of or within the reaction zone, which is arranged and constructed for either subsequent or in situ recovery of the macrocyclic compound. Alternatively, such reaction system may include multiple reaction zones and multiple recovery zones that are arranged in series, parallel, or combined forms for carrying out multi-stage reaction/recovery processes.

The recovery zone may comprise one or more separation units for selectively separating the macrocyclic compound from the reaction medium, based on differences between the macrocyclic compound and other components of the reaction medium, such as differences in one or more physical and/or chemical characteristics thereof, as for example size, shape, mass, density, solubility, volatility, permeability, diffusion rate, charge distribution, mass/charge ratio, binding affinity, adsorption/absorption potential, magnetic state, and/or reactivity. A purification unit may also be included in the recovery zone to further purify the recovered macrocyclic compound.

Such separation and/or purification arrangement may include one or more of evaporation units, flash expansion units, distillation units, stripping units, absorption units, extraction units, crystallization units, adsorption units, ion exchange units, drying units, leaching units, washing units, clathration units, osmosis units, reverse osmosis units, bubble fractionation units, magnetic separation units, chromatography units, freeze drying units, condensation units, gel filtration units, gaseous diffusion units, sweep diffusion units, thermal diffusion units, mass spectrometry units, dialysis units, electrodialysis units, gas permeation units, electrophoresis units, ultra-centrifugation units, ultra-filtration units, molecular distillation units, filtration units, demisting units, settling units, centrifugation units, cyclone flow units, and electrostatic precipitation units.

Furthermore, a recycling unit may be coupled with the reaction zone and the recovery zone, for recycling used reaction medium by collecting at least a portion of the used reaction medium from the recovery zone, treating the used reaction medium, and recirculating the treated reaction medium back to the reaction zone.

It may be desirable in some applications to further modify the macrocyclic compound for subsequent processing or ultimate use, such as by oxidation, reduction, substitution/addition/removal of functional groups, further cyclization, and/or isomeric rearrangement, and such modification can be carried out either in situ in the reaction medium within the reaction chamber, in a modification zone inside the reaction chamber, or subsequently in a modification zone downstream of the reaction chamber.

The specific arrangement and configuration of the reaction system depend on a wide variety of factors including requirements imposed by the specific reactions and products involved, and are readily determinable by a person ordinarily skilled in the art, based on the disclosure herein without undue experimentation.

The present invention can be used for synthesis of a wide variety of macrocyclic compounds, e.g., macrocyclic compounds that fit the reaction profiles illustrated in FIGS. 1A-1D. Illustrated examples of macrocyclic compounds that may be synthesized in accordance with the method of the invention include, but are not limited to, porphyrinogens, porphyrins, saphyrins, texaphyrins, bacteriochlorins, chlorins, coproporphyrin I, corrins, corroles, cytoporphyrins, deuteroporphyrins, etioporphyrin I, etioporphyrin III, hematoporphyrins, pheophorbide a, pheophorbide b, phorbines, phthalocyanines, phyllochlorins, phylloporphyrins, phytochlorins, phytoporphyrins, protoporphyrins, pyrrochlorins, pyrroporphyrins, rhodochlorins, rhodoporphyrins, uroporphyrin I, calix[n]pyrroles, calix[n]erines, cycloalkanes, cycloalkenes, cycloalkynes, piperidines, morpholines, pyrrolidines, aziridines, anilines, thiophenes, quinolines, isoquinolines, naphthalenes, pyrimidines, purines, benzofurans, oxiranes, pyrroles, thiazides, ozazoles, imidazoles, indoles, furans, benzothiophenes, polyazamacrocycles, carbohydrates, acetals, crown ethers, cyclic anhydrides, lactams, lactones, cyclic peptides, phenylthiohydantoins, thiazolinones, succinimides, coronenes, macrolides, carbocyclics, cyclodextrins, squalene oxides, ionophore antibiotics, cyclic bis-N,O-acetals, cyclic disulfides, terpenoids, spirocycles, resorcinarene macrocycles, cyclic oligo(siloxane)s, stannylated cyclic oligo(ethyleneoxide)s, cyclic poly(dibutyltindicarboxylate)s, cyclic poly(pyrrole), cyclic poly(thiophene)s, cyclic poly(amide)s, cyclic poly(ether)s, cyclic poly(carbonate)s, cyclic poly(ethersulfone)s, cyclic poly(etherketone)s, cyclic poly(urethane)s, cyclic poly(imide)s, cyclic poly(decamethylene fumarate)s, cyclic poly(decamethylethylene maleate)s, etc.

The following examples are provided to further illustrate the broad applicability of the present invention, as applicable to synthesis of a wide variety of macrocyclic compounds.

EXAMPLES

Example 1

Formation of Macrocyclic Aminomethylphosphine

Figure 5:
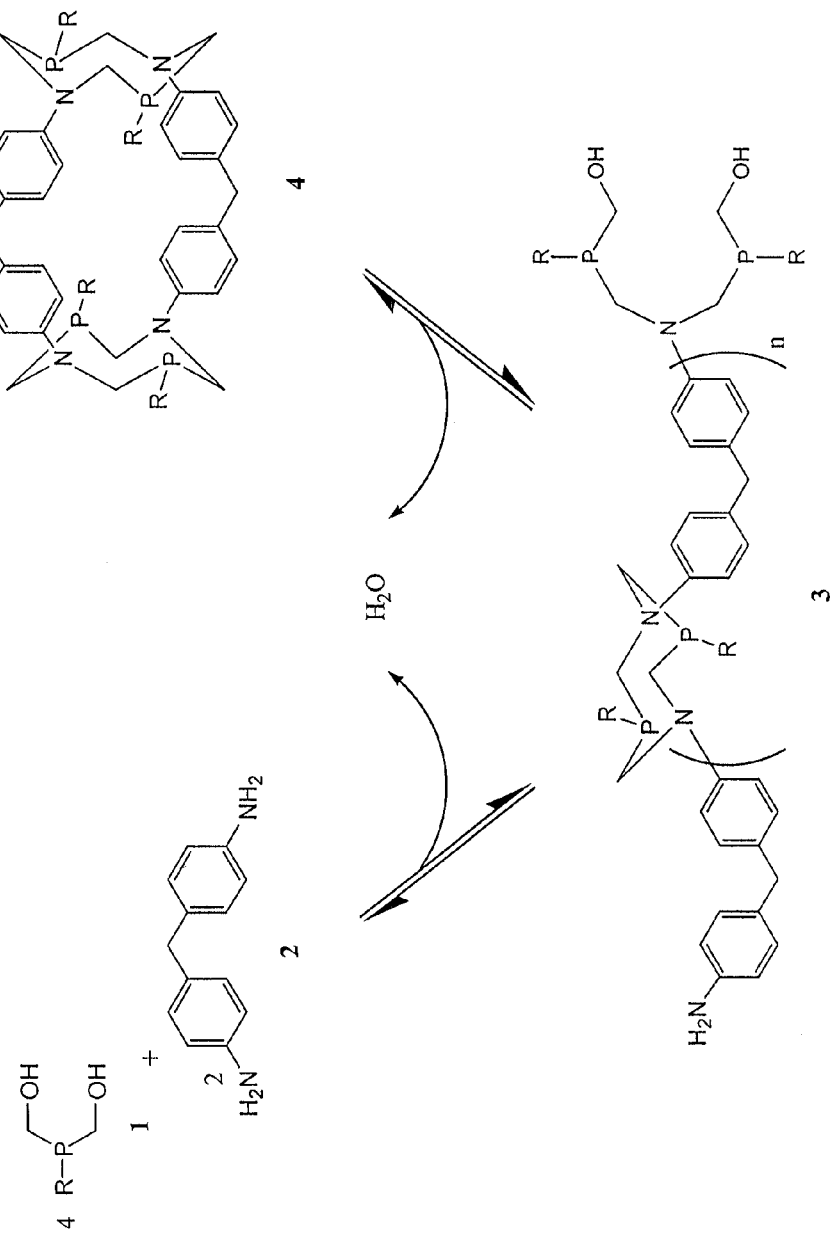
FIGS. 5-19 show processes for manufacturing a wide variety of macrocyclic compounds, according to illustrative embodiments of the present invention.

As shown in FIG. 5, two reactants can be used for forming a macrocyclic aminomethylphosphine compound. The first reactant comprises a bis(hydroxymethyl)-organylphosphine 1, and the second reactant comprises an aromatic diamine 2. The macrocyclic aminomethylphosphine compound is formed through a desired reaction pathway that comprises: (i) condensation reaction of four molecules of 1 and two molecules of 2, forming a linear intermediate product 3 with oligomerization number of two (where n=1), and cyclization of the linear intermediate product 3, forming a macrocyclic aminomethylphosphine compound 4. The intermediate product 3 is also susceptible to further undesired oligomerization in forming undesirable oligomers (where n>1).

In the practice of the present invention, the above-described reactions can be carried out in a solvent system that contains: (1) dimethylforamide (DMF) as the reacting solvent for dissolving the starting materials 1 and 2, (2) formamide as the co-solvent for facilitating phase-separation of the cyclic end product 4 from the starting materials 1 and 2, the linear intermediate product 3 (where n=1), and undesirable oligomers (where n>1), and (3) water as the oligomerization control additive to modulate formation of the undesirable oligomers. The concentrations of the starting materials 1 and 2 are preferably higher than 0.25 M. The reaction temperature is preferably within a range of from about −15° C. to about 120° C., and the reaction duration is within a range of from about 4 hours to about 60 hours.

The identity of the R group, or any substituent for that matter, may be hydrogen, aryl, phenyl, alkyl, cycloalkyl, spiroalkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; or as a protected or unprotected reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, dialkyl phosphonate, alkyl sulfonate, alkyl carboxylate, acetylacetone, and dialkyl boronate groups, or of any suitable chemical moiety appropriate to the synthesis of the macrocyclic product desired, while any two or more of R groups can be further linked together to form a loop or other intramolecular structure.

Example 2

Formation of Macrocyclic Imine

Figure 6:
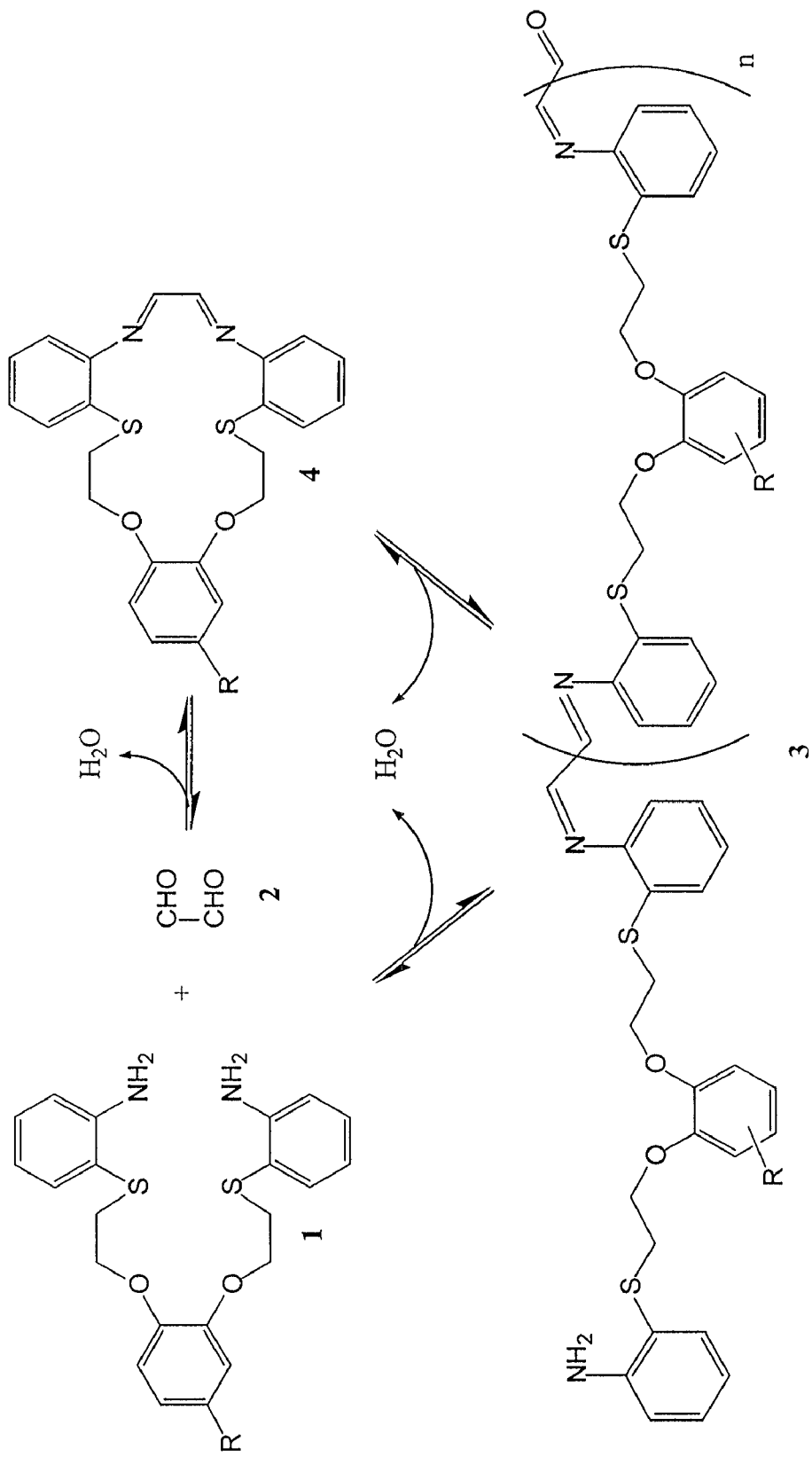

As shown in FIG. 6, two reactants 1 and 2 can be used for formation of the macrocyclic imine. The first reactant 1 comprises a diamine, and the second reactant 2 comprises a dialdehyde. Such reactants 1 and 2 form the macrocyclic imine through a desired reaction pathway that comprises: (i) condensation reaction of one molecule of 1 and one molecule of 2, forming a linear intermediate product (not shown), and (ii) cyclization of said linear intermediate product, forming a macrocyclic imine compound 4 via Schiff-base formation. The linear intermediate product is also susceptible to further undesired oligomerization in forming undesirable oligomers 3 (where $n \geqq 1$).

In the practice of the present invention, the above-described reactions can be carried out in a solvent system that contains: (1) ethanol as the reacting solvent for dissolving the starting materials 1 and 2, (2) formamide as the co-solvent for facilitating phase-separation of the cyclic end product 4 from the starting materials, the linear intermediate product, and undesired oligomers 3 (where $n \geqq 1$), and (3) water as the oligomerization control additive to modulate formation of the undesired oligomers 3. The concentrations of the starting materials 1 and 2 are preferably higher than 0.02 M. The reaction temperature is preferably within a range of from about −15° C. to about 80° C., and the reaction duration is within a range of from about 4 hours to about 60 hours. The identity of the R group is the same as described hereinabove in Example 1.

Example 3

Formation of Macrocyclic Boronate Compound

Figure 7A:
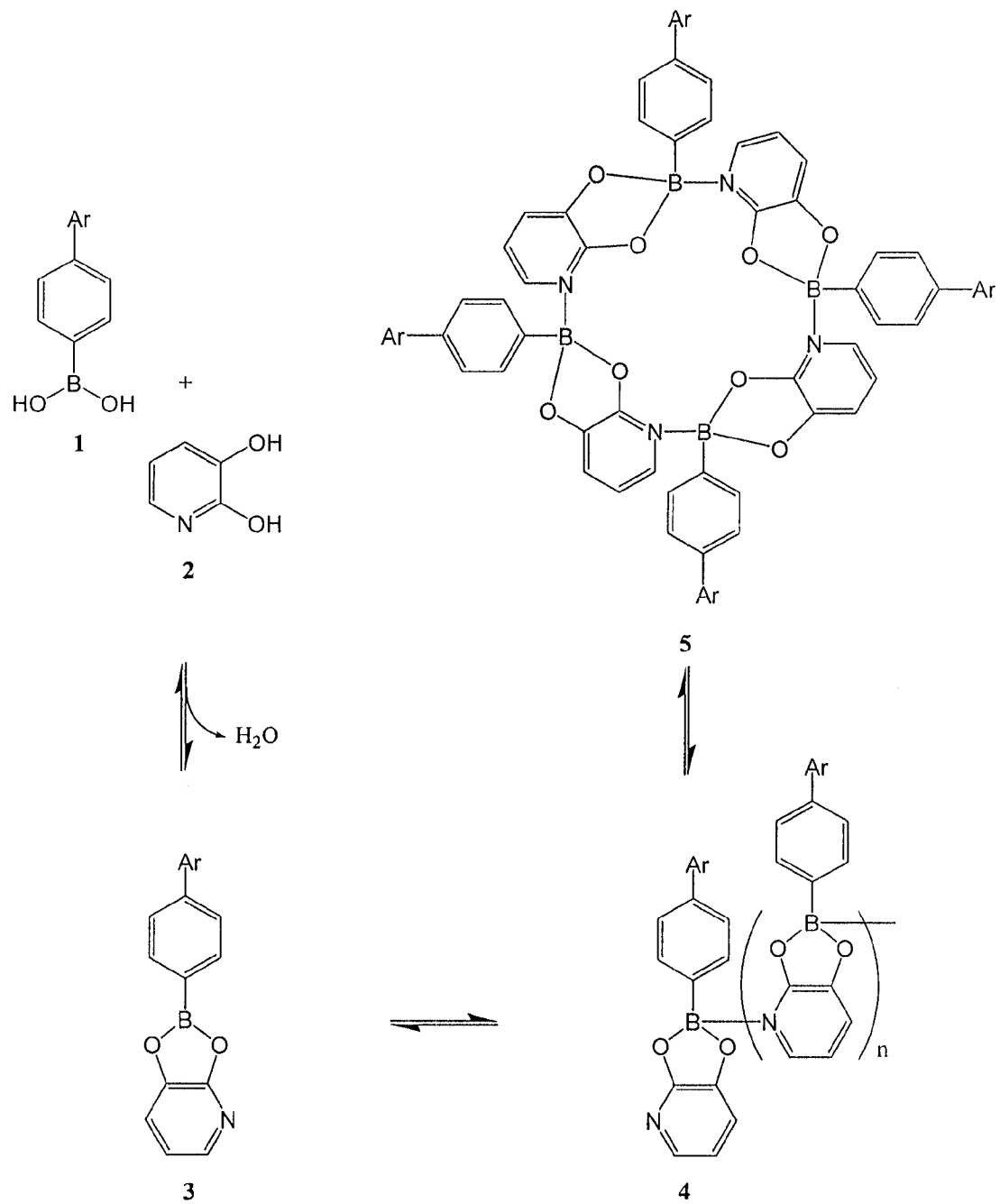

As shown in FIG. 7A, two reactants 1 and 2 can be used for forming a macrocyclic boronate compound. The first reactant 1 comprises an aryl boronic acid, and the second reactant 2 comprises a 2,3-dihydroxy-pyridine. Such reactants 1 and 2 can form the macrocyclic boronate compound through a desired reaction pathway that comprises: (i) condensation reaction of one molecule of 1 and one molecule of 2, forming a monomeric intermediate product 3, (ii) desired oligomerization of such monomeric intermediate product 3, forming a desired oligomer 4 with oligomerization number of four (where n=3), and (iii) cyclization of said desired oligomer 4, forming the desired boronate macrocyclic compound 5. Such desired oligomer 4 is susceptible to further undesired oligomerization in forming undesirable oligomers with n>3.

In practicing of the present invention, the above-described reactions can be carried out in a solvent system that contains: (1) dimethylacetamide as the reacting solvent for dissolving starting materials 1 and 2, (2) formamide as the co-solvent for facilitating phase-separation of the cyclic end product 5 from the starting materials, monomeric intermediate product 3, the desired oligomer 4 (where n=3), and undesirable oligomers (where n>3), and (3) water as the oligomerization control additive to modulate the formation of undesirable oligomers. The concentrations of the starting materials 1 and 2 are preferably higher than 0.03 M. The reaction temperature is preferably within a range of from about −15° C. to about 120° C., and the reaction duration is within a range of from about 4 hours to about 60 hours. The identity of the Ar group is the same as described hereinabove for the R group in Example 1. In this reaction, the added water breaks the boron-oxygen bond in the oligomers 4 and therefore modulates the oligomerization reactions.

Example 4

Alternative Process for Formation of Macrocyclic Boronate Compound

Figure 7B:
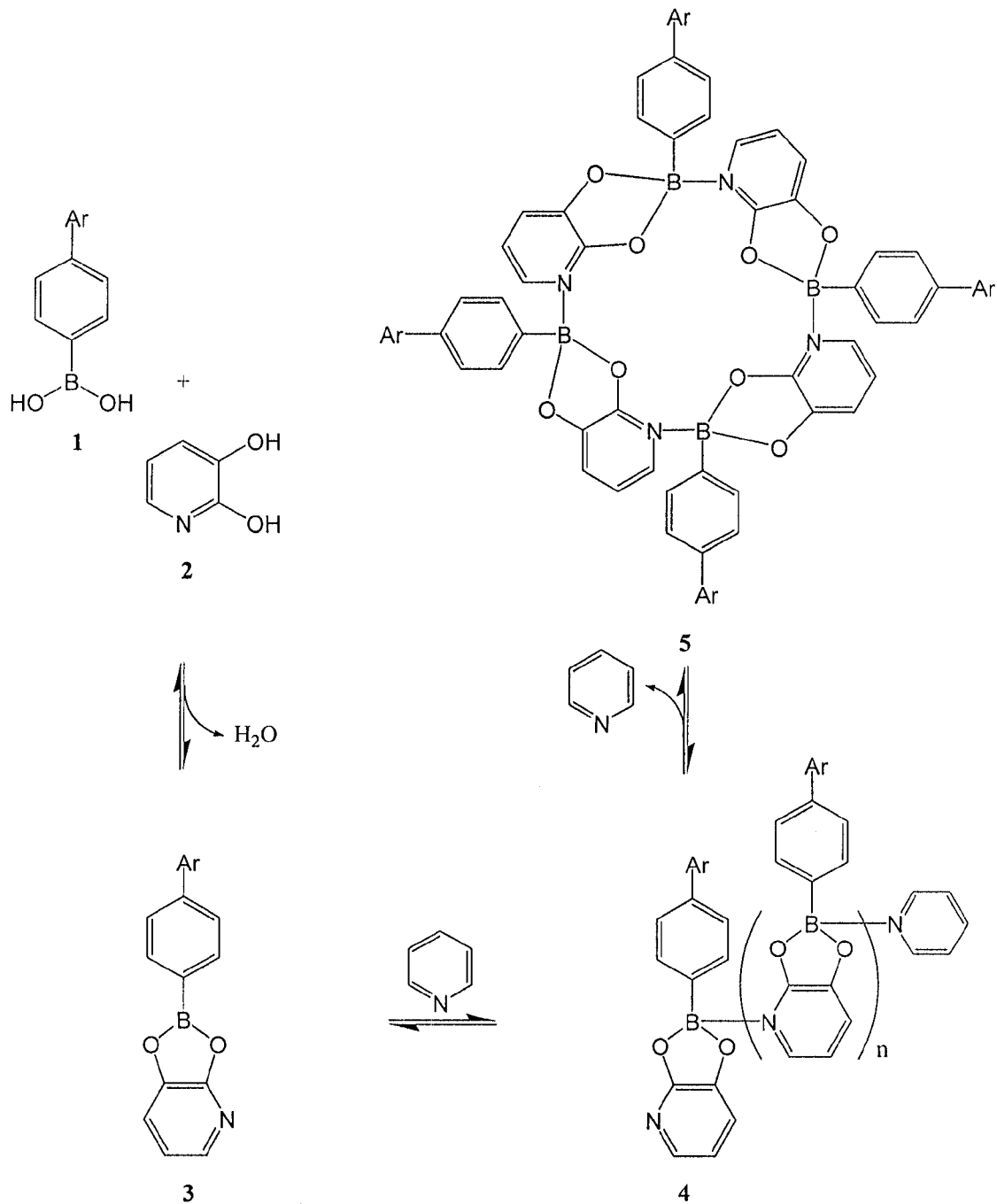

FIG. 7B shows an alternative process for forming the macrocyclic boronate compound in addition to the process described in FIG. 7A, wherein the same reactants 1 and 2 can be used for forming the macrocyclic boronate compound in the same manner as described in Example 3, with the exception that pyridine, instead of water, is used as the oligomerization control additive to modulate formation of the undesirable oligomers. In this reaction, the added pyridine interrupts formation of the boron-nitrogen required for oligomerization and therefore modulates the oligomerization reactions. Pyridine as used herein provides additional control over the oligomerization reactions, which is not available in FIG. 7A.

Further, a mixture of pyridine and water can be used as the oligomerization control additives for more effective modulation of the oligomerization reactions. It is also within the scope of the present invention to add pyridine and remove water for controlling the oligomerization reactions. Removal of water drives the condensation reaction and prevents decomposition of the monomeric intermediate 3. Further, it prevents hydrolysis of the boron-oxygen bonds in the oligomers and limits the oligomer decomposition to the extent only caused by boron-nitrogen bond disruption.

Example 5

Formation of Macrocyclic Calix[4]Pyrrole Compound

Figure 8A:
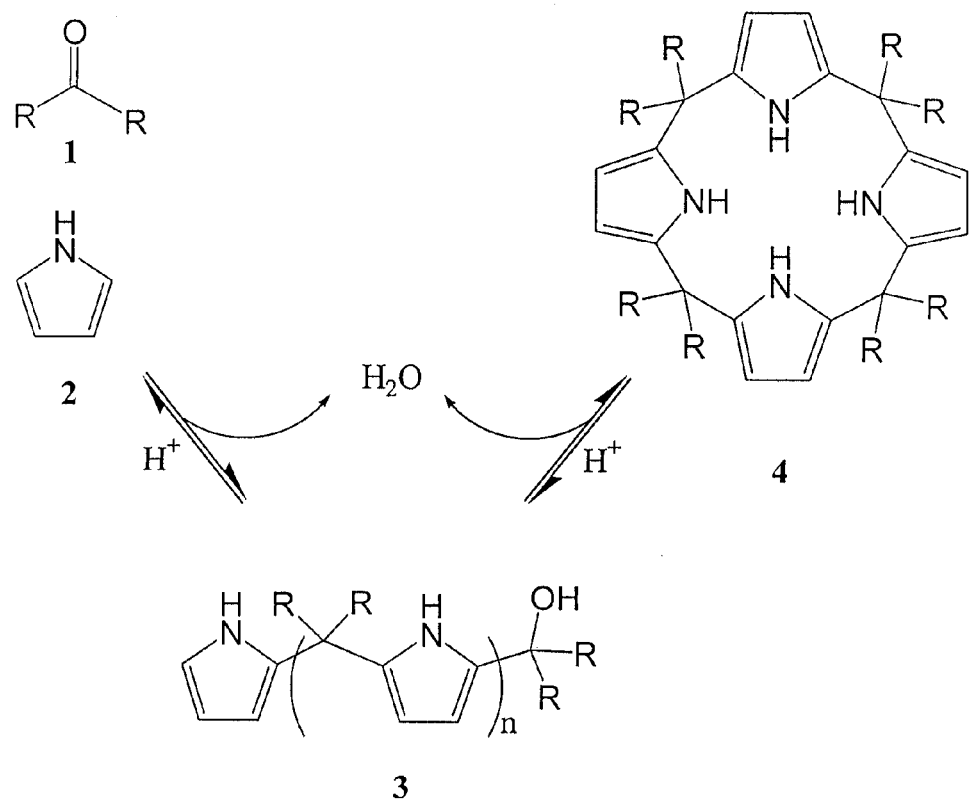

As shown in FIG. 8A, two reactants 1 and 2 can be used for forming the macrocyclic calix[4]pyrrole compound. Specifically, the first reactant 1 comprises a ketone, and the second reactant 2 comprises a pyrrole, which can form the macrocyclic calix[4]pyrrole compound through a desired reaction pathway that comprises: (i) condensation reaction of 1 and 2, forming a monomeric intermediate product (not shown); (2) desired oligomerization of such monomeric intermediate, forming a desired oligomer 3 with oligomerization number of four (where n=3); and (iii) cyclization of said desired oligomer 3, forming the macrocyclic calix[4]pyrrole compound 4. Such desired oligomer 3 is also susceptible to further undesired oligomerization in forming undesirable oligomers with n>3.

In practicing of the present invention, the above-described reactions can be carried out in a solvent system that contains: (1) dimethylacetamide as the reacting solvent for dissolving starting materials 1 and 2, (2) formamide as the co-solvent for facilitating phase-separation of the cyclic end product 4 from the starting materials 1 and 2, the desired oligomer 3 (where n=3), and undesirable oligomers (where n>3), and (3) water as the equilibrium control agent to modulate formation of the undesirable oligomers. The concentrations of the starting materials 1 and 2 are preferably higher than 0.01 M. The reaction temperature is preferably within a range of from about −15° C. to about 120° C., and the reaction duration is within a range of from about 4 hours to about 60 hours. The identity of the R group is the same as described hereinabove in Example 1.

Example 6

Alternative Process for Formation of Macrocyclic Calix[4]Pyrrole Compound

Figure 8B:
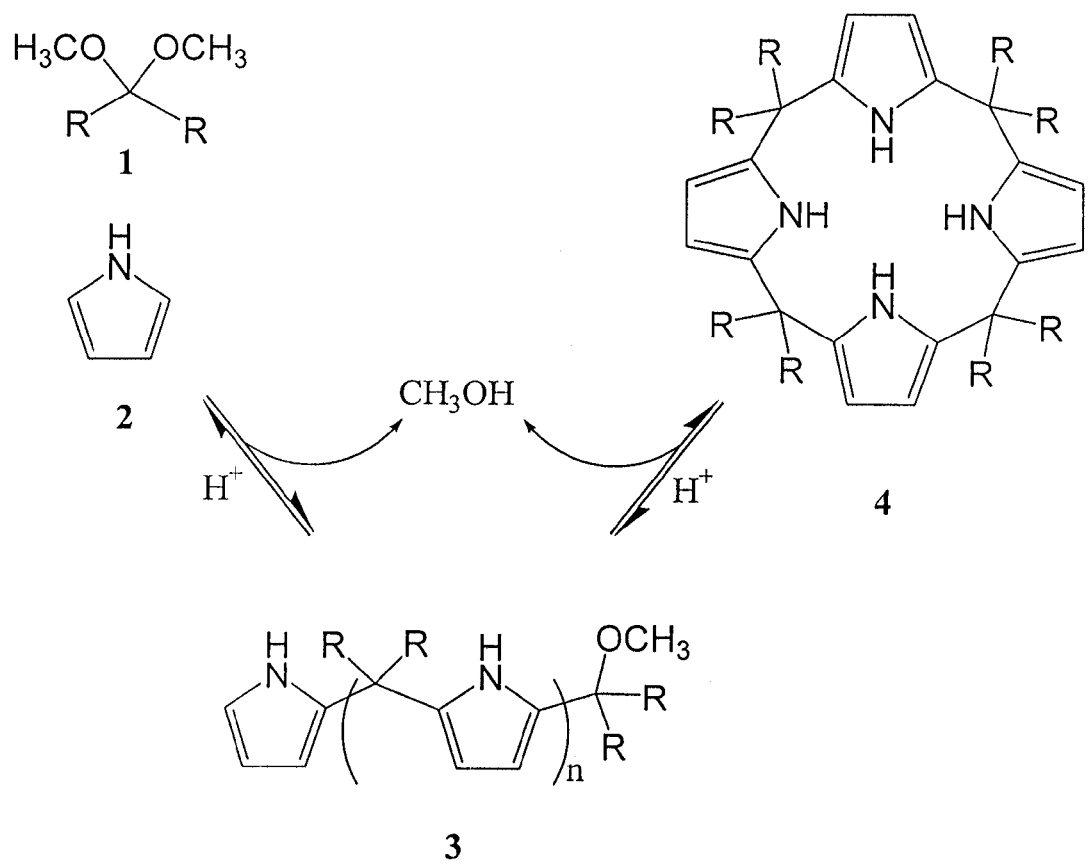

FIG. 8B shows an alternative process for forming the macrocyclic calix[4]pyrrole compound in addition to the process described in FIG. 8A, wherein a different reactant 1 is used, which causes generation of a different oligomerization byproduct (i.e., methanol instead of water). Consequently, methanol, instead of water, is used as the oligomerization control additive to modulate formation of the undesirable oligomers.

This example shows that by manipulating the starting materials, different oligomerization byproducts can be generated, enabling oligomerization control by different oligomerization control additives, and one ordinarily skilled in the art can readily select the suitable starting materials and the oligomerization control additives for optimizing the macrocyclic production, consistent with the principle and spirit of the present invention.

Example 7

Formation of Macrocyclic Crown Ether

Figure 9:
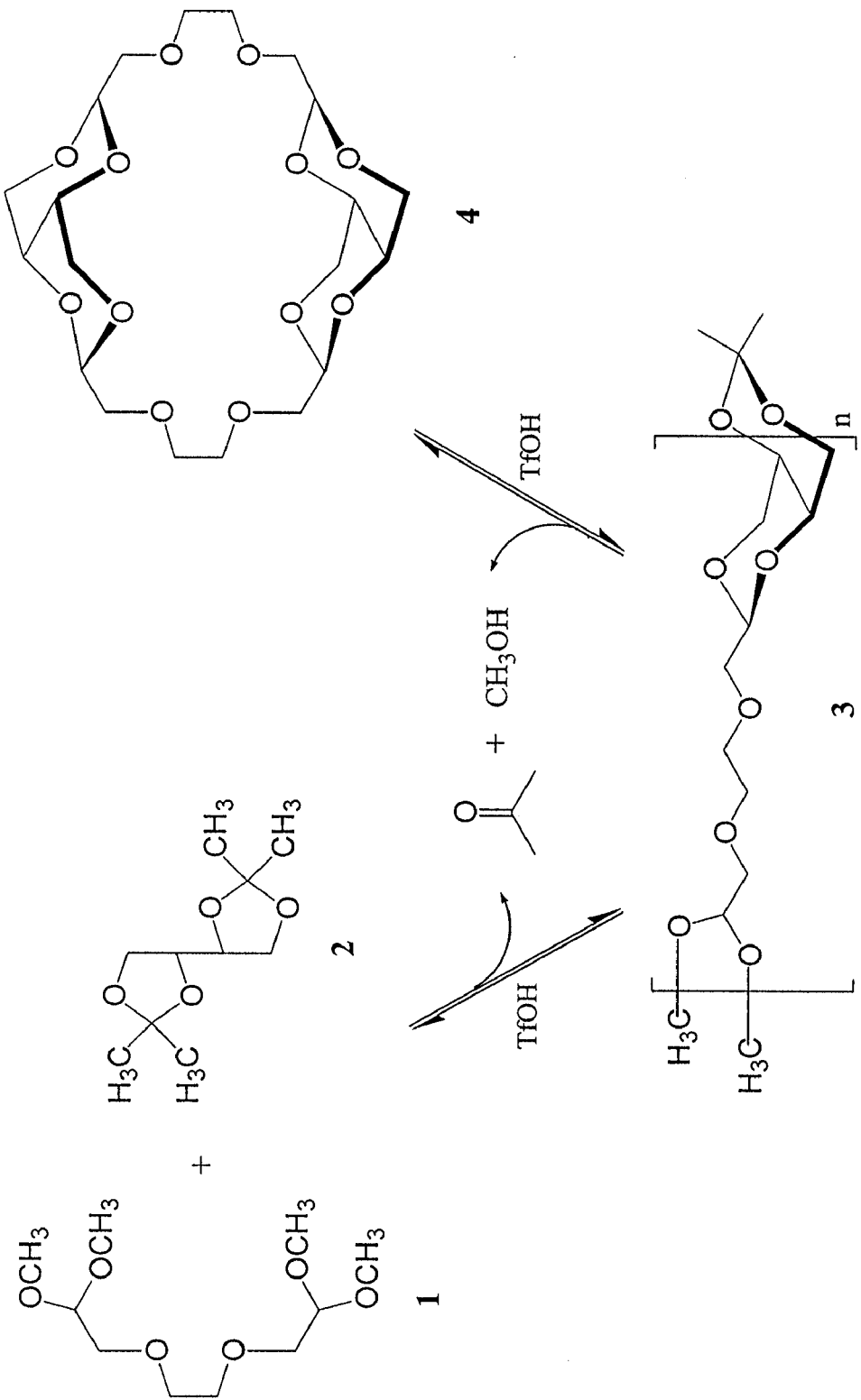

As shown in FIG. 9, two reactants 1 and 2 can be used for formation of the macrocyclic crown ether. The first reactant 1 comprises a diacetal, and the second reactant 2 comprises a diacetonide, which can form the macrocyclic crown ether through a desired reaction pathway that comprises: (i) condensation reaction of one molecule of 1 and one molecule of 2, forming a monomeric intermediate product (not shown); (ii) oligomerization of such monomeric intermediate product, forming a desired oligomer 3 with oligomerization number of two (where n=2), and (iii) cyclization of the desired oligomer 3, forming the macrocyclic crown ether compound 4. Such desired oligomer 3 is also susceptible to further undesired oligomerization in forming undesirable oligomers (wherein n>2).

In practice of the present invention, the above-described reactions can be carried out in a solvent system that contains: (1) acetonitrile as the reacting solvent for dissolving the starting materials 1 and 2, (2) formamide as the co-solvent for facilitating phase-separation of the cyclic end product 4 from the starting materials 1 and 2, the desired oligomer 3 (where n=2), and undesirable oligomers (where n>2), and (3) a mixture of acetone and methanol as the equilibrium control agents to modulate formation of the undesirable oligomers. The concentrations of the starting materials 1 and 2 are preferably higher than 0.04M. The reaction temperature is preferably within a range of from about −15° C. to about 60° C., and the reaction duration is within a range of from about 4 hours to about 72 hours.

Example 8

Formation of Cyclic Peptide

Figure 10:
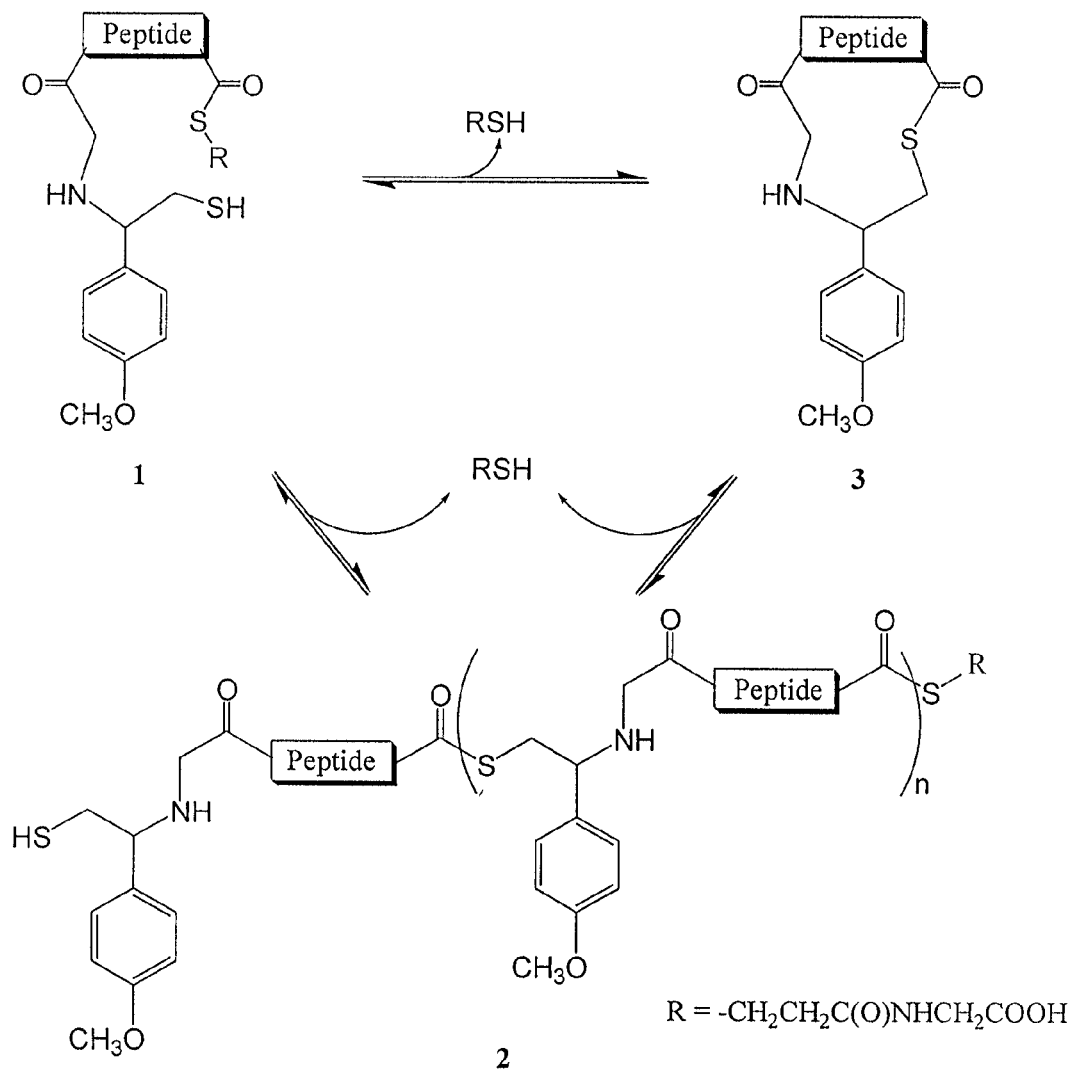

As shown in FIG. 10, a single reactant 1 that comprises a peptide chain flanked by a terminal thioester group and a terminal thiol group is used for formation of a cyclic peptide 3 with a thiolactone linker through cyclization of such reactant. The reactant 1 is susceptible of undesired self-oligomerization in forming undesirable oligomers 2 (where n≧1).

In practice of the present invention, the above-described reaction can be carried out in a solvent system that contains: (1) an aqueous 0.2 M sodium phosphate pH 7.4 buffer as the reacting solvent for dissolving the starting material 1, and (2) thiophenol as the equilibrium control agent to modulate formation of undesired oligomers 2. The concentration of the starting material 1 is preferably higher than 0.001 M. The reaction temperature is preferably within a range of from about −15° C. to about 100° C., and the reaction duration is within a range of from about 2 hours to about 48 hours. No co-solvent is used herein. Instead, solvent removal process is used for facilitating phase-separation of the cyclic end product 3 from the starting material 1 and the undesired oligomers 2. The identity of the R group is —CH2CH2C(O)NHCH2COOH, but may it be any suitable chemical moiety appropriate to the synthesis of the product desired.

Example 9

Formation of Imidazolium-Linked Bicyclic Compound

Figure 11:
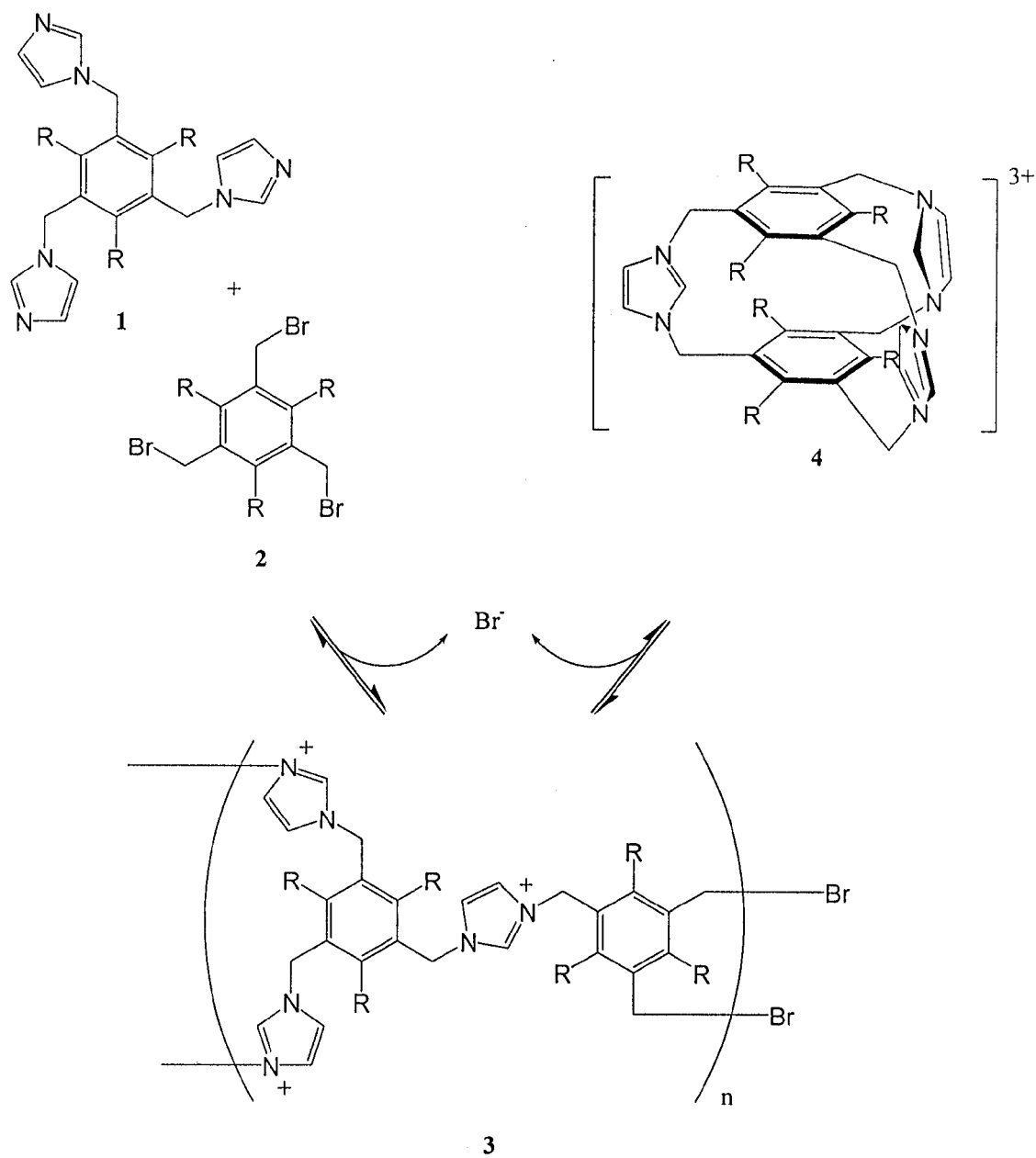

As shown in FIG. 11, two reactants 1 and 2 can be used for forming an imidazolium-linked bicyclic compound. Specifically, the first reactant 1 comprises an (imidazol-1-ylmethyl) benzene, and the second reactant 2 comprises a (bromomethyl)benzene, which can form the imidazolium-linked bicyclic compound through a desired reaction pathway that comprises: (i) condensation reaction of one molecule of 1 and one molecule of 2, forming a linear intermediate product (not shown); (ii) cyclization of said linear intermediate production, forming a cyclic intermediate product with one ring structure (not shown); and (iii) further cyclization of the cyclic intermediate product to form the imidazolium-linked bicyclic compound 4 with two ring structures. The linear intermediate product is susceptible to undergo undesired oligomerization in forming undesired linear oligomers 3 (where n>1), and the cyclic intermediate product is also susceptible to undesired oligomerization in forming undesired oligomers (not shown) with ring structures.

In practicing the present invention, the above-described reactions can be carried out in a solvent system that contains: (1) dimethylformamide as the reacting solvent for dissolving the starting materials 1 and 2, (2) acetone as the co-solvent for facilitating phase-separation of the cyclic end product 4 from the starting materials, the linear and cyclic intermediate products, the undesired linear oligomers 3 (where n>1), and the undesirable oligomers with ring structures, and (3) bromide as the equilibrium control agent to modulate formation of the undesirable oligomers, either linear or with ring structures. The concentrations of the starting materials 1 and 2 are preferably higher than 0.03 M. The reaction temperature is preferably within a range of from about −15° C. to about 120° C., and the reaction duration is within a range of from about 4 hours to about 168 hours. The identity of the R group is methyl, but it may be of any suitable chemical moiety appropriate to the synthesis of the product desired as listed in Example 1.

Example 10

Formation of Macrocyclic Lactone

Figure 12:
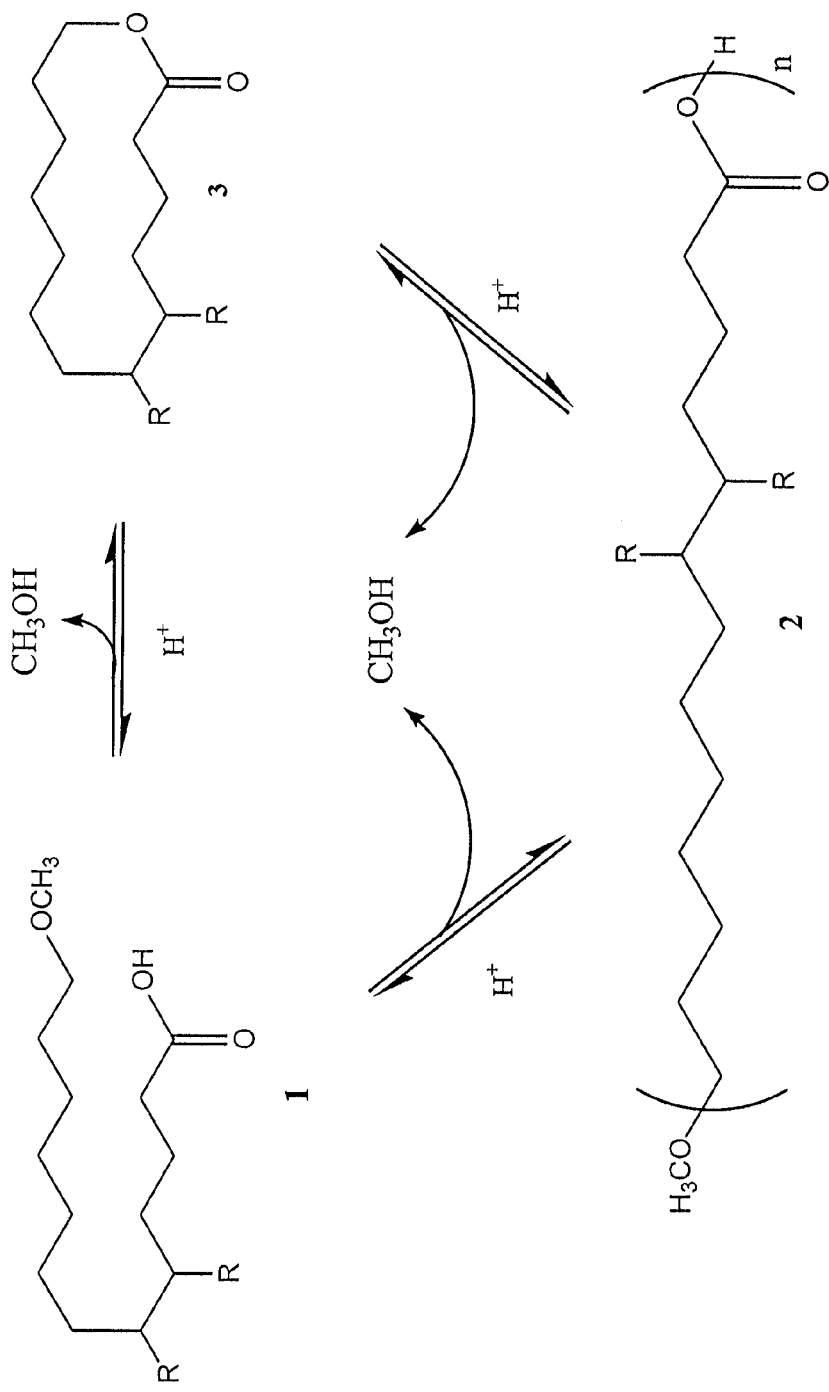

As illustrated in FIG. 12, a single reactant 1 that comprises a carboxylic acid terminal group and an ether terminal group can be used for forming the macrocyclic lactone compound 2 through cyclization. Such reactant 1 is susceptible of undesired self-oligomerization in forming undesirable oligomers 3. The identity of the R group is the same as described hereinabove in Example 1.

In practicing the present invention, the above-described reaction can be carried out in a solvent system that contains: (1) dimethylacetamide as the reacting solvent for dissolving the starting material 1, (2) formamide as the co-solvent for facilitating phase-separation of the cyclic end product 2 from the starting material 1 and the undesirable oligomers 3 (where n>1), and (3) methanol as the equilibrium control agent to modulate formation of the oligomers. The concentration of the starting material 1 is preferably higher than 0.1 M. The reaction temperature is preferably within a range of from about −15° C. to about 120° C., and the reaction duration is within a range of from about 4 hours to about 72 hours.

Example 13

Formation of Arylene Ethynylene Macrocycle

Figure 13:
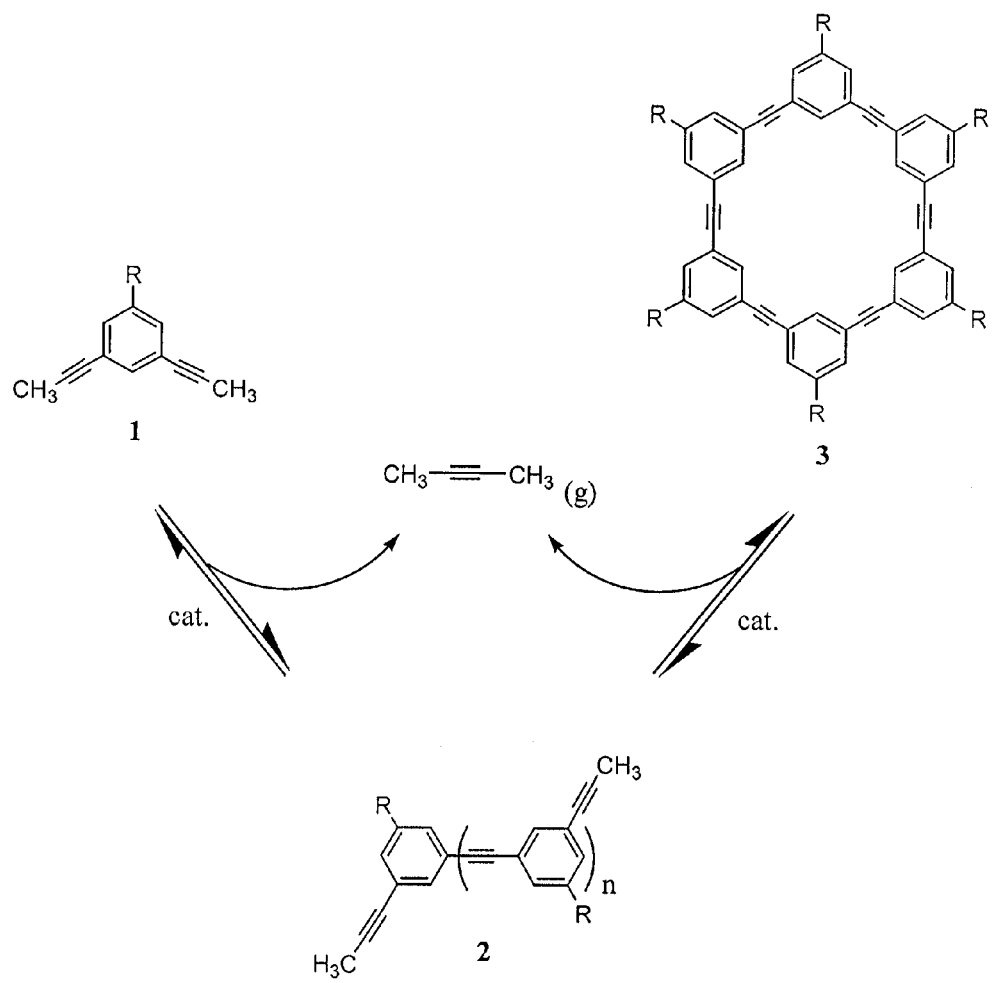

As shown in FIG. 13, a single reactant 1 that comprises a dialkyne can be used for forming the arylene ethynylene macrocyclic compound 2 through a desired reaction pathway that comprises: (i) oligomerization reaction of six molecules of 1, forming a desired oligomer 3 with oligomerization number of six (where n=5) that is susceptible to further undesired oligomerization in forming undesirable oligomers with n>5, and (ii) cyclization of said desired oligomer 3, forming an arylene ethynylene macrocyclic compound.

In the present invention, this reaction can be carried out in a solvent system that contains: (1) $CCl_4$ as the reacting solvent for dissolving the starting material 1 and catalyst system, (2) nitrobenzene as the co-solvent for facilitating phase-separation of the cyclic end product 2 from the starting material 1, the desired oligomer 3 (where n=5), and the undesired oligomers (where n>5), and (3) 2-butyne as the equilibrium control agent to modulate formation of the undesired oligomers. The concentration of the starting material 1 is preferably higher than 0.04 M. The reaction temperature is preferably within a range of from about −15° C. to about 80° C., and the reaction duration is within a range of from about 4 hours to about 24 hours.

Alternatively, this reaction can be carried out in a solvent system that contains: (1) $CH_2Cl_2$ as the reacting solvent for dissolving the starting material 1 and catalyst system, and (2) 2-butyne as the equilibrium control agent to modulate formation of the undesirable oligomers. The concentration of the starting material 1 is preferably higher than 0.04 M. The reaction temperature is preferably within a range of from about −15° C. to about 80° C., and the reaction duration is within a range of from about 4 hours to about 24 hours. No co-solvent is used. Instead, solvent removal method is used for facilitating phase-separation of the cyclic end product 2 from the starting materials, linear intermediate product 3, where n=5 and the undesired oligomers 3, where n>5.

Example 14

Formation of the Macrocyclic Compound Via Mixed Aldol Reaction

Figure 14:
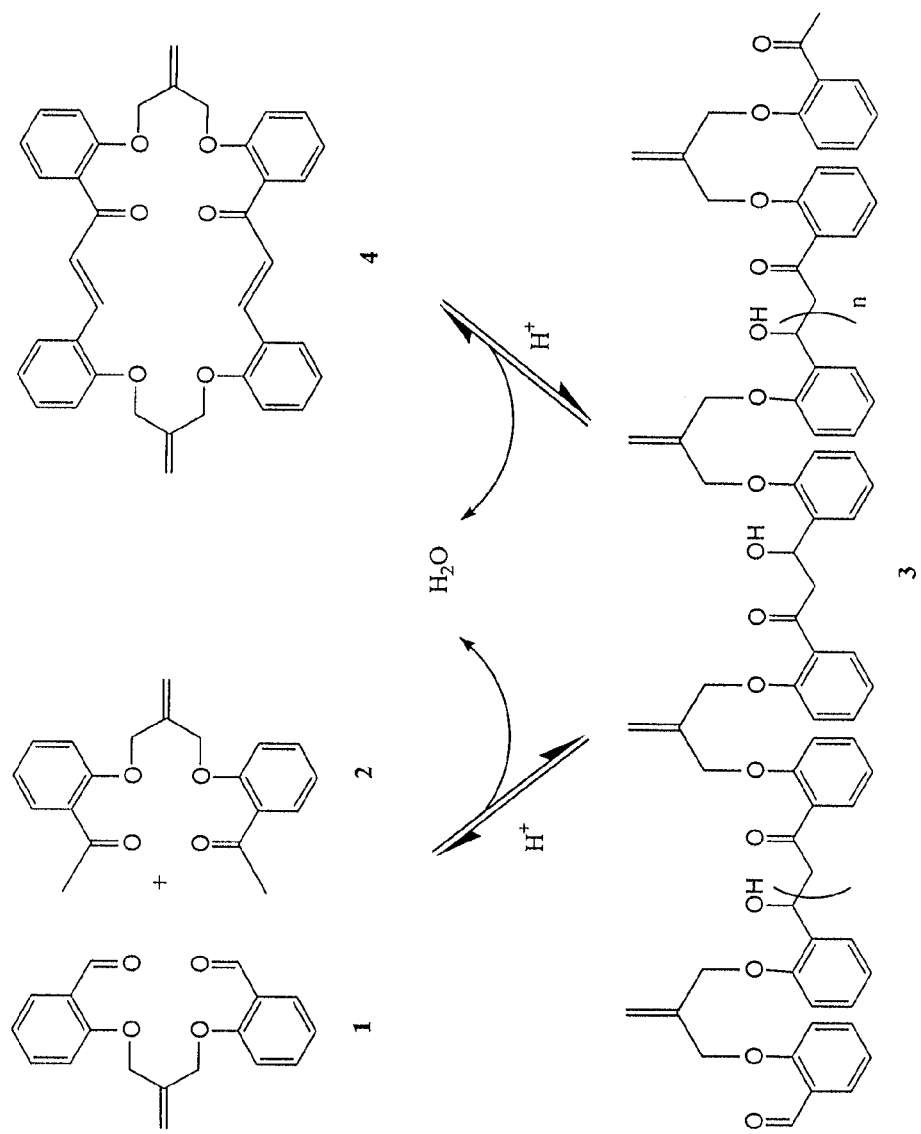

As shown in FIG. 14, two reactants 1 (a dialdehyde) and 2 (a diketone) are used for forming a macrocyclic compound through a desired reaction pathway that comprises: (i) condensation reaction of one molecule of said first reactant and one molecule of said second reactant, forming a linear intermediate product 3 with oligomerization number of two that is susceptible to further undesired oligomerization in forming undesirable oligomers, and (ii) cyclization of said linear intermediate product, forming a macrocyclic compound via a mixed Aldol reaction.

In the present invention, this reaction is carried out in a solvent system that contains: (1) dimethylacetamide as the reacting solvent for dissolving the starting materials 1 and 2, (2) formamide as the co-solvent for facilitating phase-separation of the cyclic end product 4 from the starting materials, linear intermediate product 3, where n=0, and undesired oligomers where n>0, and (3) water as the equilibrium control agent to modulate formation of the undesirable oligomers where n>0. The concentration of the starting materials 1 and 2 is preferably higher than 0.1 M. The reaction temperature is preferably within a range of from about −15° C. to about 80° C., and the reaction duration is within a range of from about 4 hours to about 60 hours.

Example 15

Formation of Porphyrinogen

Figure 15:
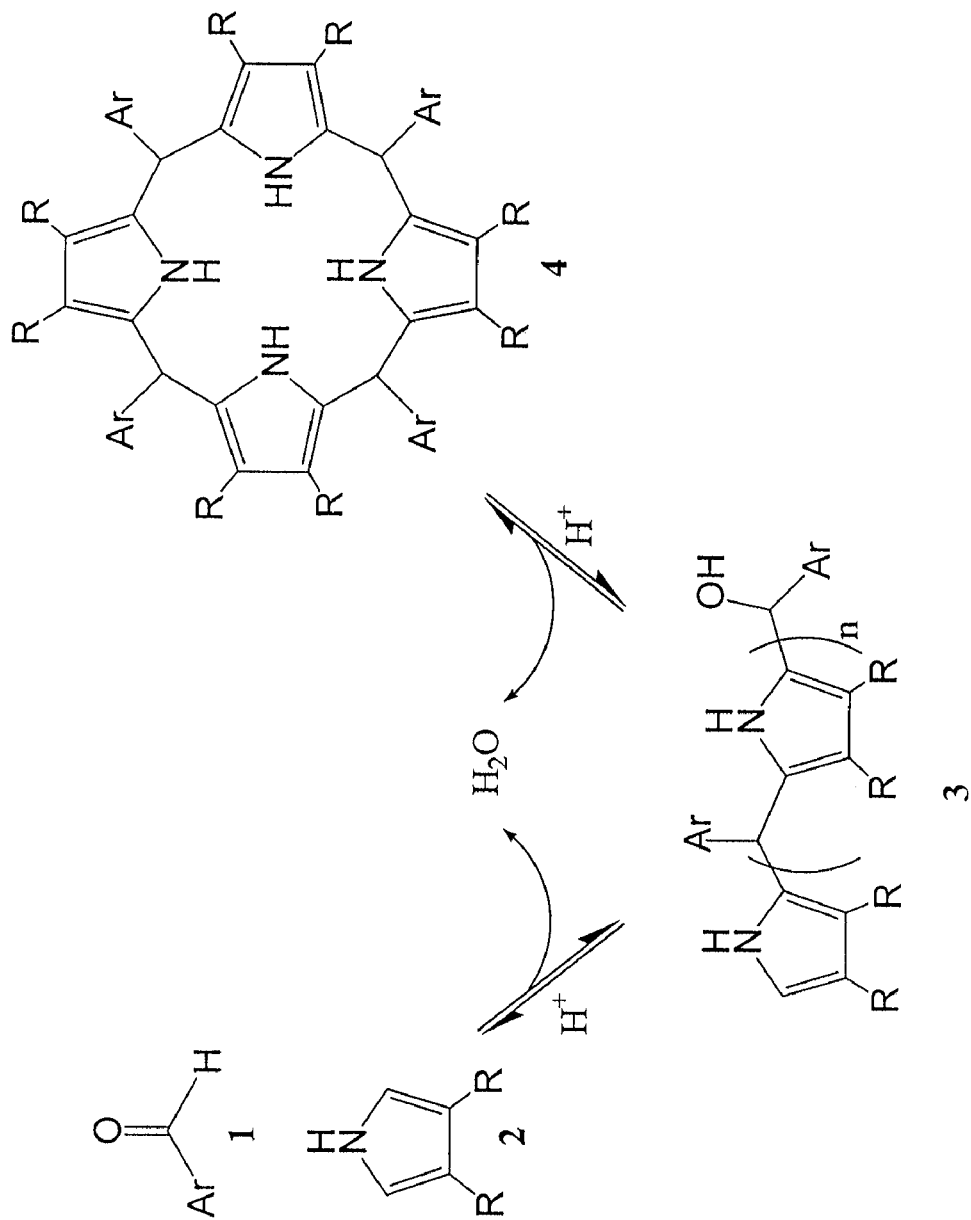

As shown in FIG. 15, a macrocyclic porphyrinogen can be formed by using two reactants 1 (an aldehyde) and 2 (a pyrrole) through a desired reaction pathway that comprises: (i) condensation reaction of four molecules of 1 and four molecules of 2, forming a linear intermediate product with oligomerization number of four that is susceptible to further undesired oligomerization in forming undesirable oligomers, and (ii) cyclization of said linear intermediate product, forming a macrocyclic porphyrinogen compound.

In the present invention, this reaction can be carried out in a solvent system that contains: (1) dimethylacetamide as the reacting solvent for dissolving starting materials 1 and 2, (2) formamide as the co-solvent for facilitating phase-separation of the cyclic end product 4 from the starting materials, linear intermediate product 3, where n=3, and the undesired oligomers where n>3, and (3) water as the equilibrium control agent to modulate formation of the undesired oligomers 3, where n>3. The concentration of the starting materials 1 and 2 is preferably higher than 0.01 M. The reaction temperature is preferably within a range of from about −15° C. to about 120° C., and the reaction duration is within a range of from about 4 hours to about 60 hours. The identity of the Ar group is 4-(iodo)phenyl and the R group is H, but, may be of any suitable chemical moiety appropriate to the synthesis of the product desired.

Example 16

Formation of Resorcinarene

Figure 16:
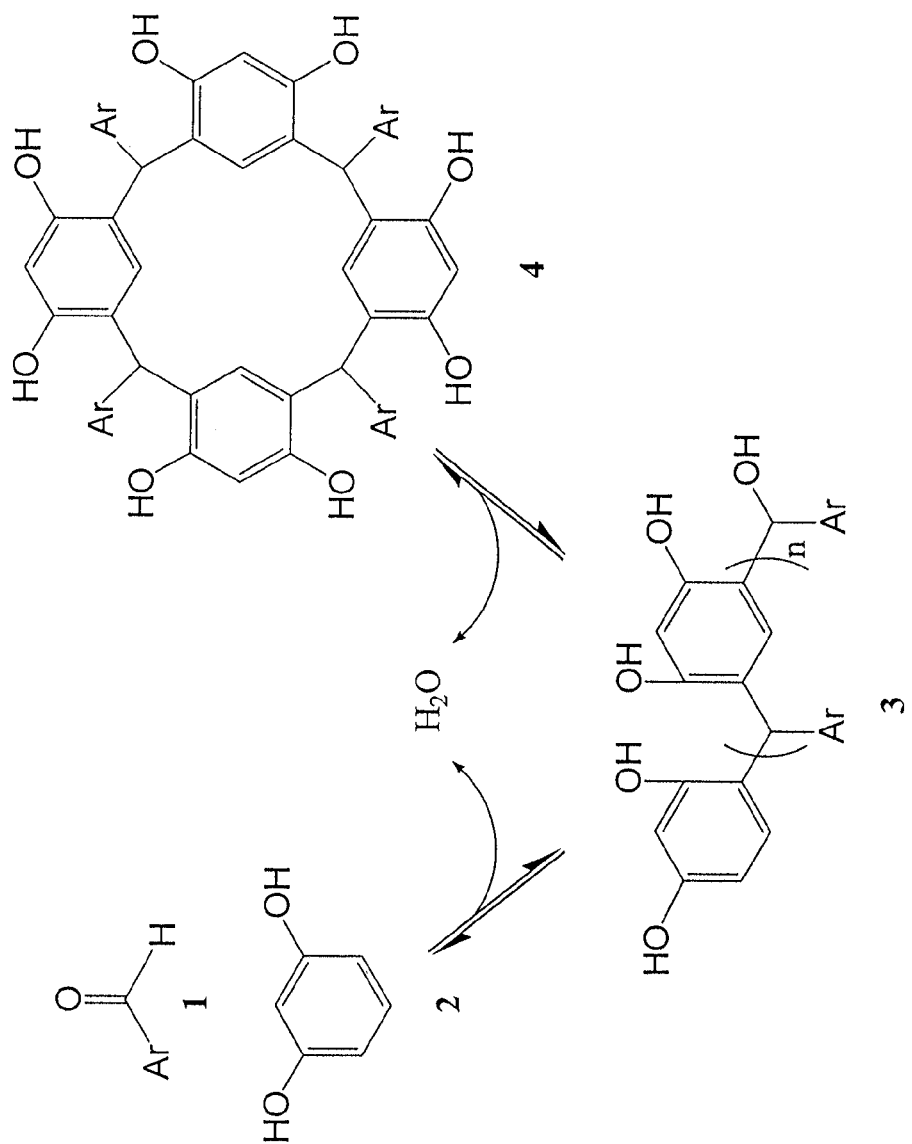

As shown in FIG. 16, a macrocyclic resorcinarene can be formed by using two reactants 1 (an aldehyde) and 2 (a resorcinol) through a desired reaction pathway that comprises: (i) condensation reaction of four molecules of 1 and four molecules of 2, forming a linear intermediate product with oligomerization number of four that is susceptible to further undesired oligomerization in forming undesirable oligomers, and (ii) cyclization of said linear intermediate product, forming a macrocyclic resorcinarene compound.

In the present invention, this reaction can be carried out in a solvent system that contains: (1) dimethylacetamide as the reacting solvent for dissolving starting materials 1 and 2, (2) formamide as the co-solvent for facilitating phase-separation of the cyclic end product 4 from the starting materials, linear intermediate product 3, where n=3, and undesired oligomers 3, where n>3, and (3) water as the equilibrium control agent to modulate formation of the undesired oligomers 3, where n>3. The concentration of the starting materials 1 and 2 is preferably higher than 0.01 M. The reaction temperature is preferably within a range of from about −15° C. to about 120° C., and the reaction duration is within a range of from about 4 hours to about 60 hours. The identity of the Ar group is p-tolyl, but, may be of any suitable chemical moiety appropriate to the synthesis of the product desired as listed in Example 1.

Example 17

Formation of Macrocyclic Heteroheptaphyrin

Figure 17:
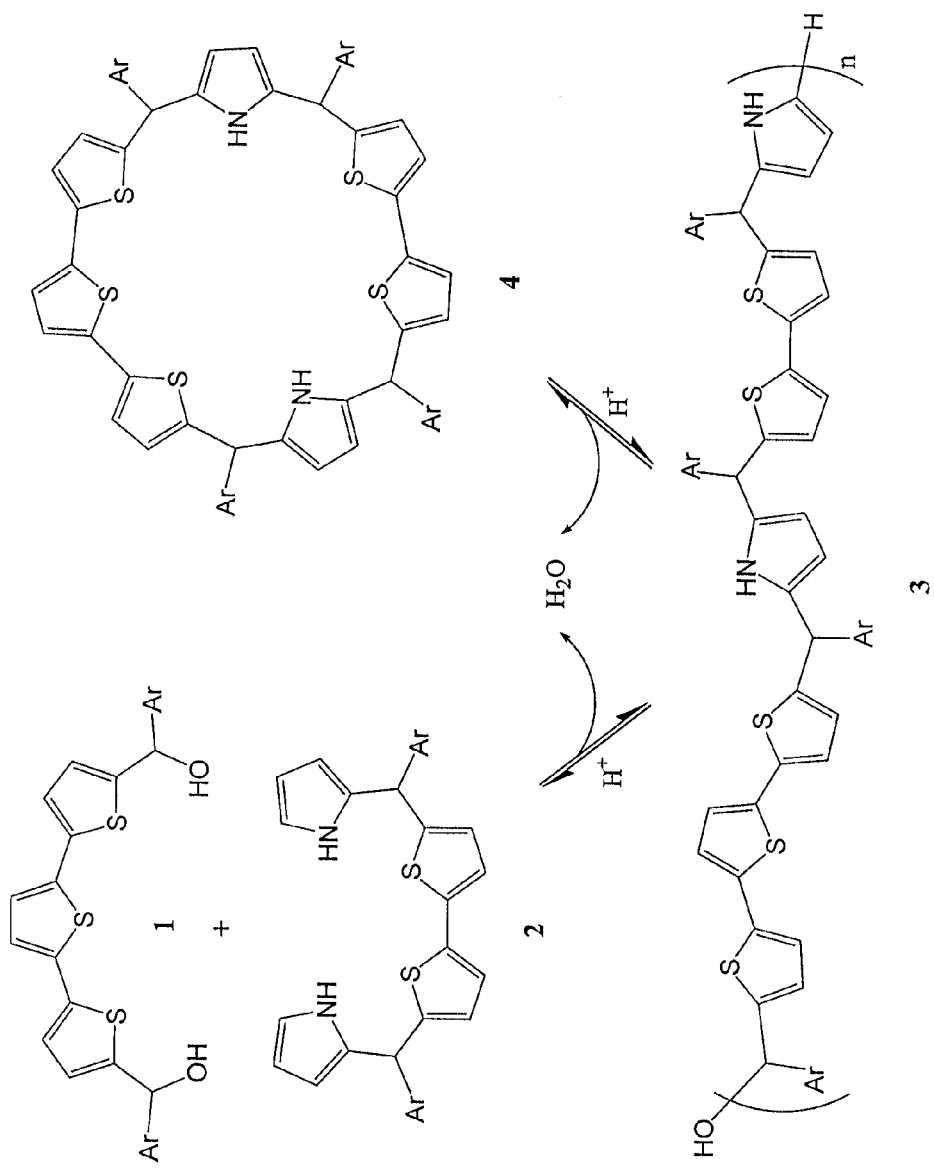

As shown in FIG. 17, a macrocyclic heteroheptaphyrin compound can be formed by two reactants 1 (a trithiophenediol) and 2 (a linear heterotetrapyrrole) through a desired reaction pathway that comprises: (i) condensation reaction of one molecule of 1 and one molecule of 2, forming a linear intermediate product with oligomerization number of one that is susceptible to further undesired oligomerization in forming undesirable oligomers, and (ii) cyclization of said linear intermediate product, forming a macrocyclic heteroheptaphyrin compound.

In the present invention, this reaction is carried out in a solvent system that contains: (1) dimethylacetamide as the reacting solvent for dissolving starting materials 1 and 2, (2) formamide as the co-solvent for facilitating phase-separation of the cyclic end product 4 from the starting materials, linear intermediate product 3, where n=1, and undesired oligomers 3, where n>1, and (3) water as the equilibrium control agent to modulate formation of the undesired oligomers 3, where n>1. The concentration of the starting materials 1 and 2 is preferably higher than 0.01 M. The reaction temperature is preferably within a range of from about −15° C. to about 120° C., and the reaction duration is within a range of from about 4 hours to about 60 hours. The identity of the Ar group is Mesityl, but, may be of any suitable chemical moiety appropriate to the synthesis of the product desired as listed in Example 1.

Example 18

Formation of Macrocyclic Thioether Sulfone Compound

Figure 18:
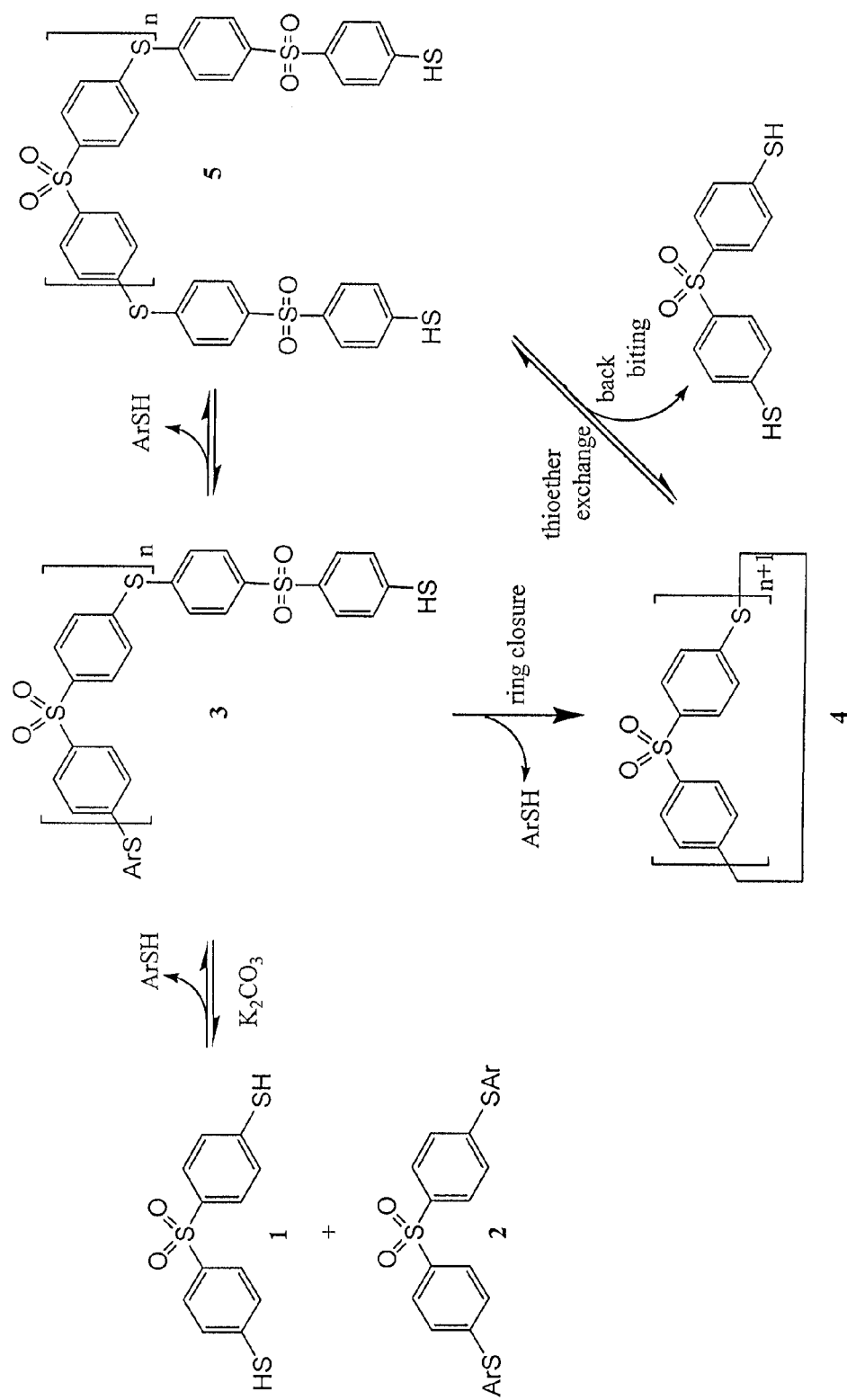

As shown in FIG. 18, a macrocyclic thioether sulfone compound can be formed by using two reactants 1 (a bisthiophenol) and 2 (a bisthiophenylether) through a desired reaction pathway that comprises: (i) condensation reaction of two molecules of said first reactant and two molecules of said second reactant, forming a linear intermediate product with oligomerization number of two that is susceptible to further undesired oligomerization in forming undesirable oligomers, and (ii) cyclization of said linear intermediate product, forming a macrocyclic aromatic thioether sulfone compound via thioether exchange.

In the present invention, this reaction can be carried out in a solvent system that contains: (1) benzene as the reacting solvent for dissolving the starting materials 1 and 2, (2) dimethylacetamide as the co-solvent for facilitating phase-separation of the cyclic end product 4, where n=4, from the starting materials, linear intermediate product 3, where n=3, linear intermediate 5, where n≧3, and the undesirable oligomers 3, where n>3 and 5, where n>>3, and (3) thiophenol as the equilibrium control agent to modulate formation of the undesirable oligomers 3 and 5. The concentration of the starting material 1 is preferably higher than 0.1 M. The reaction temperature is preferably within a range of from about −15° C. to about 100° C., and the reaction duration is within a range of from about 4 hours to about 72 hours. The identity of the Ar group is phenyl, but, may be of any suitable chemical moiety appropriate to the synthesis of the product desired as listed in Example 1.

Example 19

Formation of Macrocyclic Dibutyltin Dicarboxylate Compound

Figure 19:
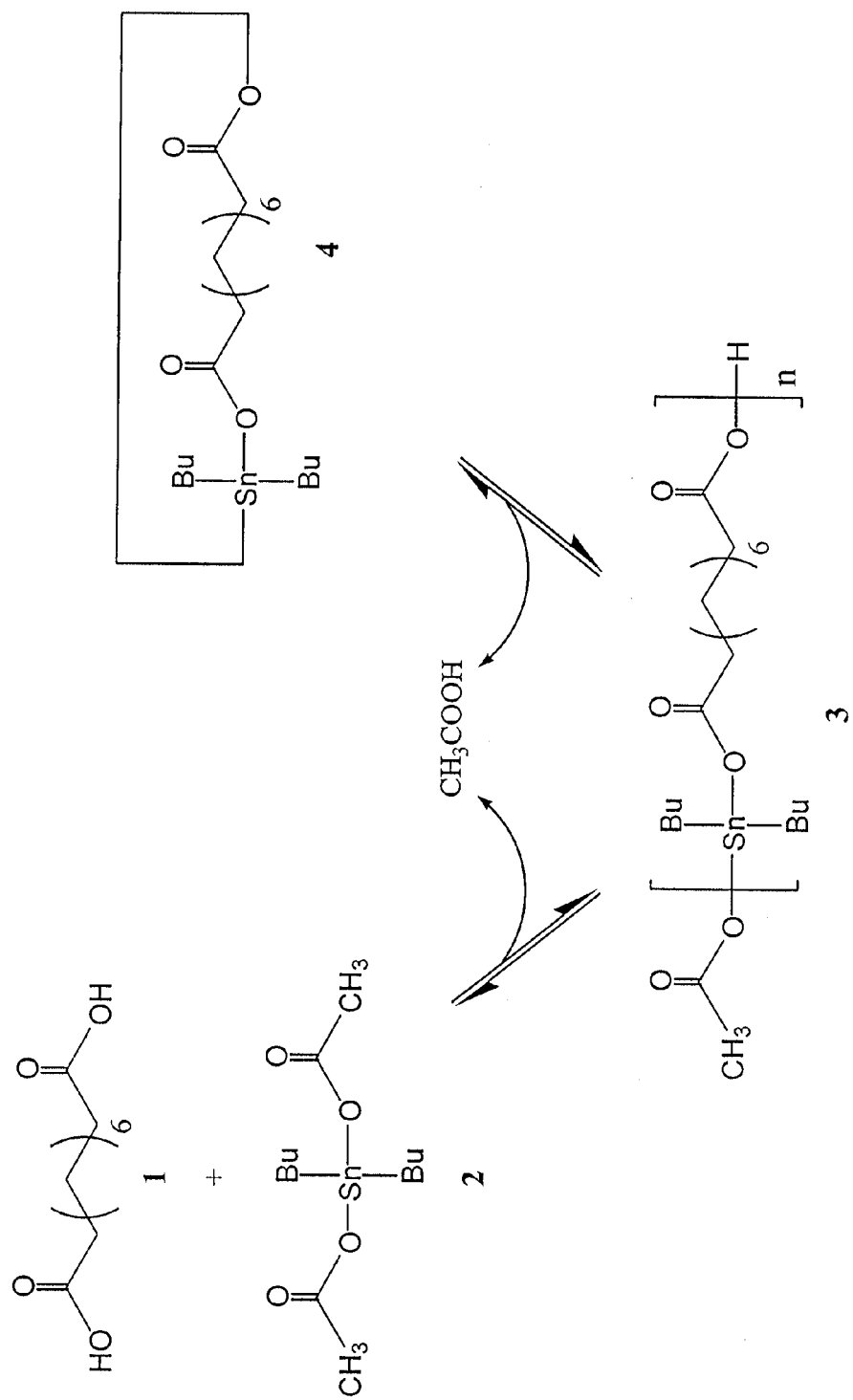

As shown in FIG. 19, a macrocyclic dibutyltin dicarboxylate compound can be formed by using two reactants 1 (a dicarboxylic acid) and 2 (a dibutyltin bisacetate) through a desired reaction pathway that comprises: (i) condensation reaction of one molecule of 1 and one molecule of 2, forming a linear intermediate product with oligomerization number of one that is susceptible to further undesired oligomerization in forming undesirable oligomers, and (ii) cyclization of said linear intermediate product, forming a macrocyclic dibutyltin dicarboxylate compound.

In the present invention, this reaction can be carried out in a solvent system that contains: (1) chlorobenzene as the reacting solvent for dissolving the starting materials 1 and 2, (2) dimethylacetamide as the co-solvent for facilitating phase-separation of the cyclic end product 4 from the starting materials, linear intermediate product 3, where n=1, and undesired oligomers 3, where n>1, and (3) acetic acid as the equilibrium control agent to modulate formation of undesired oligomers 3, where n>1. The concentration of the starting materials 1 and 2 is preferably higher than 0.4 M. The reaction temperature is preferably within a range of from about −15° C. to about 120° C., and the reaction duration is within a range of from about 4 hours to about 72 hours.

While the invention has been described herein with reference to a wide variety of specific embodiments, it will be appreciated that the invention is not thus limited, and extends to and encompasses a wide variety of other modifications and embodiments, as will be appreciated by those ordinarily skilled in the art. Accordingly, the invention is intended to be construed and interpreted broadly, in accordance with the ensuing claims.

The invention claimed is:
1. A cyclization process, comprising:
 a) providing a reaction system comprising one or more reactants in a reaction medium, wherein:
  (i) at least one of the reactants is a linear precursor that participates in an oligomerization process, which oligomerization process produces, in addition to oligomers, one or more oligomerization byproducts,

(ii) the oligomerization process proceeds to a desired degree of oligomerization to form a desired oligomer before the desired oligomer can be either cyclized to form a desired cyclic product, or undergo further oligomerization to form one or more undesired oligomers, and (iii) the degree of oligomerization can be controlled in such a manner as to increase yields of the desired oligomer, and decrease yields of said one or more undesired oligomers, by adding a first amount of said one or more extraneous reaction byproducts, and can increase yields of at least one of said one or more undesired oligomers, and decrease yields of said desired oligomer, by adding a second amount of said one or more extraneous reaction byproducts, b) adding said first amount of said one or more extraneous oligomerization byproducts into the reaction medium, so as to increase oligomerization to said desired degree to form said desired oligomer, and decrease further oligomerization to form said undesired oligomer(s), relative to the amount of further oligomerization that would be observed in a corresponding reaction medium to which said one or more extraneous oligomerization byproducts is not added, or said second amount of said one or more oligomerization byproducts is added; and c) cyclizing the desired oligomer to form a desired cyclic reaction product.

2. The process of claim 1 wherein one of the reactants comprises a pyrrole.

3. The process of claim 1, wherein the product comprises a compound selected from the group consisting of porphyrinogens, porphyrins, saphyrins, texaphyrins, bacteriochlorins, chlorins, coproporphyrin I, corrins, corroles, cytoporphyrins, deuteroporphyrins, etioporphyrin I, etioporphyrin III, hematoporphyrins, pheophorbide a, pheophorbide b, phorbines, phthalocyanines, phyllochlorins, phylloporphyrins, phytochlorins, phytoporphyrins, protoporphyrins, pyrrochlorins, pyrroporphyrins, rhodochlorins, rhodoporphyrins, and uroporphyrin I.

4. The process of claim 1, wherein the product comprises a cyclic peptide.

5. The process of claim 1, wherein the product comprises a macrocyclic lactone.

6. The process of claim 1, wherein the product comprises a macrolide.

7. The process of claim 1, wherein the cyclic reaction product includes an oxidizable functional group, further comprising:

d) oxidizing the cyclic reaction product.

8. The process of claim 1, further comprising:

d) purifying the cyclic reaction product.

9. The process of claim 1, wherein the cyclic reaction product includes a reduceable functional group, further comprising:

d) reducing the cyclic reaction product.

10. The process of claim 1, wherein the cyclic reaction product includes functional groups capable of further cyclization, further comprising:

d) further cyclizing the cyclic reaction product.

11. The process of claim 1, wherein the cyclic reaction product includes functional groups capable of isomeric rearrangement, further comprising:

d) subjecting the cyclic reaction product to isomeric rearrangement.

* * * * *